(12) United States Patent
Harris

(10) Patent No.: US 8,170,405 B2
(45) Date of Patent: May 1, 2012

(54) MULTIPURPOSE CARTRIDGE-BASED LIQUID DISPENSING AIR FRESHENER SYSTEM

(76) Inventor: Robert M. Harris, Roseville, CA (US)

( * ) Notice: Subject to any disclaimer, the term of this patent is extended or adjusted under 35 U.S.C. 154(b) by 531 days.

(21) Appl. No.: 12/412,401

(22) Filed: Mar. 27, 2009

(65) Prior Publication Data
US 2010/0243754 A1  Sep. 30, 2010

(51) Int. Cl.
*F24F 3/14* (2006.01)
*A01G 13/06* (2006.01)
(52) U.S. Cl. ......... 392/392; 392/386; 392/387; 392/463
(58) Field of Classification Search ........... 392/386–464
See application file for complete search history.

(56) References Cited

U.S. PATENT DOCUMENTS

| | | | | |
|---|---|---|---|---|
| 4,601,886 A * | 7/1986 | Hudgins | ...................... | 422/116 |
| 4,603,030 A * | 7/1986 | McCarthy | ...................... | 472/57 |
| 4,629,604 A * | 12/1986 | Spector | ...................... | 422/124 |
| 5,111,477 A * | 5/1992 | Muderlak et al. | ............. | 392/390 |
| 5,167,877 A * | 12/1992 | Pai | ................ | 261/18.1 |
| 5,259,062 A * | 11/1993 | Pelonis | ......................... | 392/365 |
| 5,591,409 A * | 1/1997 | Watkins | ........................ | 422/110 |
| 6,443,434 B1* | 9/2002 | Prather | ........................... | 261/26 |
| 6,619,559 B2* | 9/2003 | Wohrle | ............................ | 239/34 |
| 6,783,117 B2* | 8/2004 | Wohrle | ............................ | 261/26 |
| 6,859,615 B2* | 2/2005 | Yip et al. | ...................... | 392/395 |
| 6,950,607 B2* | 9/2005 | Yip et al. | ...................... | 392/395 |
| 7,152,809 B2* | 12/2006 | Ketcha et al. | .................... | 239/13 |
| 7,223,166 B1* | 5/2007 | Wiseman et al. | ............. | 454/337 |
| 7,493,028 B2* | 2/2009 | DeWitt et al. | ................. | 392/395 |
| 7,734,159 B2* | 6/2010 | Beland et al. | ................. | 392/390 |
| 2002/0066798 A1* | 6/2002 | Laudamiel-Pellet et al. | ... | 239/34 |
| 2005/0094988 A1* | 5/2005 | Yip et al. | ...................... | 392/395 |
| 2005/0167860 A1* | 8/2005 | Brooks | .......................... | 261/81 |
| 2005/0205916 A1* | 9/2005 | Conway et al. | ............... | 257/299 |
| 2005/0226788 A1* | 10/2005 | Hrybyk et al. | ................ | 422/124 |
| 2006/0193611 A1* | 8/2006 | Ruiz Ballesteros et al. | .. | 392/394 |
| 2006/0291828 A1* | 12/2006 | Kadoma et al. | ............... | 392/404 |
| 2008/0085103 A1* | 4/2008 | Beland et al. | ................. | 392/390 |

* cited by examiner

*Primary Examiner* — Thor Campbell

(57) ABSTRACT

A high-performance, modular, multipurpose, cartridge-based, liquid dispensing air freshener system that uses at least one refillable or disposable liquid filled cartridge. It can also use fixed tanks and dispense pesticides or any other liquid that can be vaporized. This programmable device can use an unlimited number of cartridges to discharge numerous different fragrances of which can be dispensed separately or mixed. A variety of chassis size and shape configurations can be used, such as a micro-sized unit that allows extreme portability so that it can be used in cars, at office desks or easily carried around in a pocket or purse; it can also function as a compact plug-in air freshener. Cartridges can be automatically selected so that the system can dispense a different scent for different time intervals or mix scents. It can be built into an automotive dash panel or designed to fit into a car style stereo slot.

23 Claims, 25 Drawing Sheets

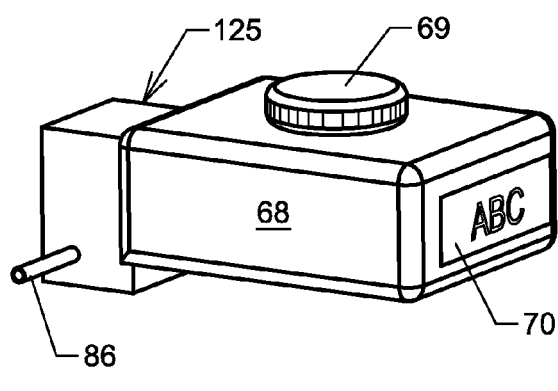
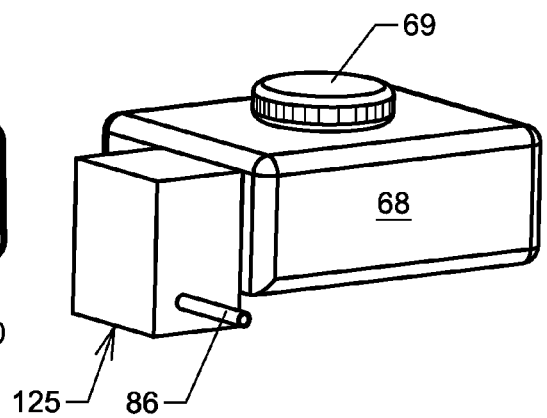
FIG. 29   FIG. 30
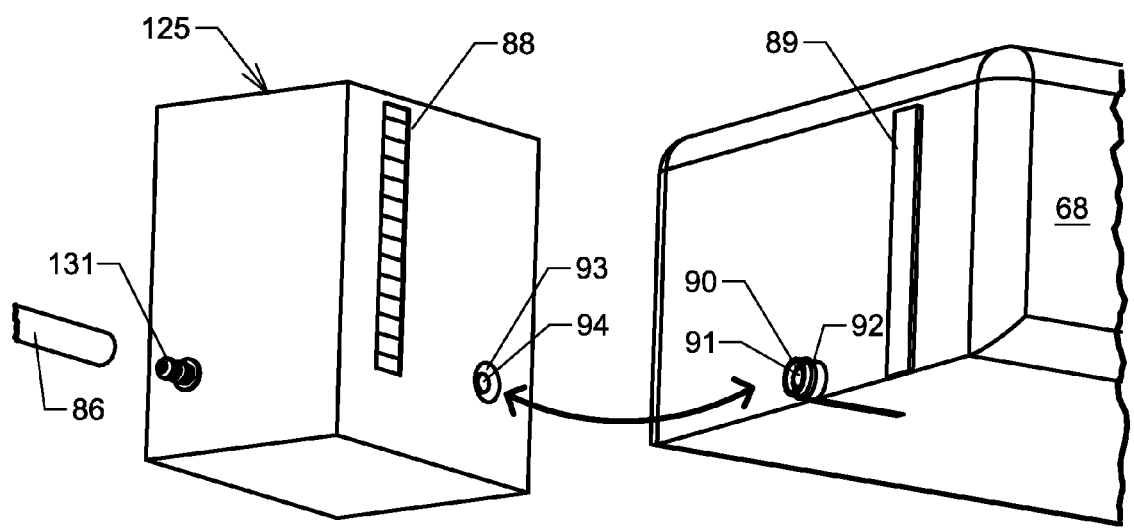
FIG. 31

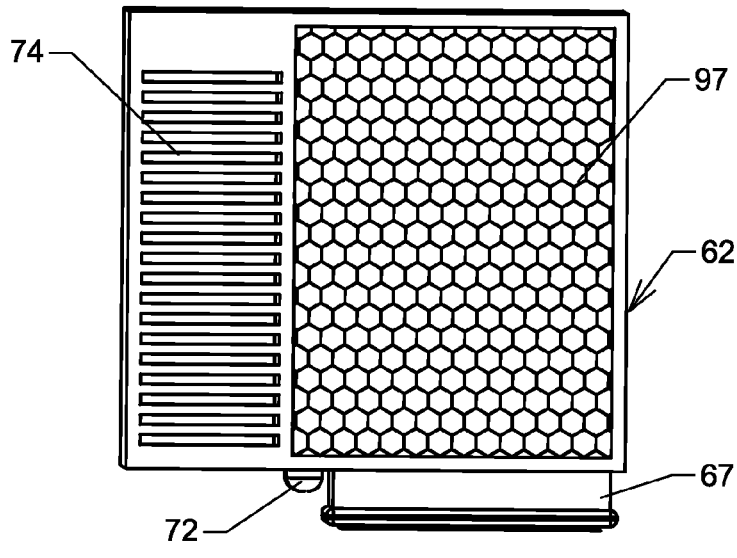
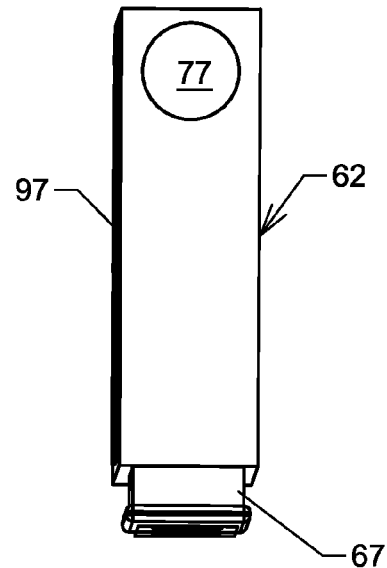
FIG. 35  FIG. 36
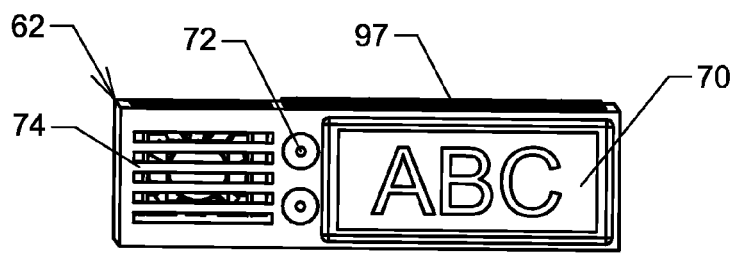
FIG. 37
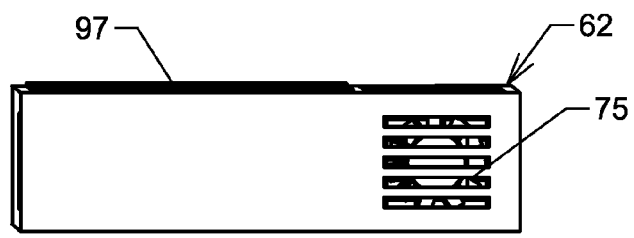
FIG. 38

MULTIPURPOSE CARTRIDGE-BASED LIQUID DISPENSING AIR FRESHENER SYSTEM

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of the Invention

The present invention relates in general to air freshener devices and more particularly to a high-performance, multi-purpose cartridge-based liquid dispensing air freshener, of which can be used in many ways by using various special chassis adaptations.

2. Description of the Prior Art

There is a desire to make the ambient air more pleasing in personal living spaces, professional office settings and in motor vehicles where the atmosphere within such confined spaces contains unpleasant odors from such things as smoking, cooking and pets. Additionally, there is a desire for insect and pest control in these spaces and is an ongoing need.

It can be appreciated that air fresheners have been in use for years. Devices for producing such a scent or fragrance are well known in the prior art, and have been extensively used indoors and in vehicles. The prior art describes many of such devices that may be employed for use in these spaces for both air freshening and insect control. These devices encompass a myriad of designs by the crowded prior art that have been developed for the fulfillment of countless objectives and requirements.

The disadvantage with many air freshener devices is that the fragrance-producing material is quickly depleted or consumed whereby a strong fragrance is generated for a short time. Furthermore, some prior devices have not been refillable, and therefore in order to maintain the emission of fragrance for a long period of time, it has been necessary to replace the entire device.

Various types of dispensing devices have been devised and used in which an aerosol material is intermittently discharged as a spray into a room by either a clock mechanism that forms a part of the device or an electrically operated valve that is also included as an integral part of the dispenser. The disadvantages of these devices is that the pressurized aerosol liquid and dispensers used therewith are relatively expensive, are bulky and provide only a periodic dispensing very high concentrations of fragrance for very short bursts.

Many other prior art describe devices that provide electrical heating devices for dispensing such materials as air fresheners, deodorizers, and insect control materials. Such devices may often comprise a reservoir of liquid to be dispensed, an electric heater to warm the liquid to cause it to vaporize more readily, and an electrical plug to plug the device into an electric outlet for power. These devices have very little to no control over the fragrance output, where the device continuously works as long as it is plugged in.

While these devices fulfill their respective, particular objectives and requirements, the aforementioned patents do not disclose the unique combination of components and features of the present invention that substantially departs from the conventional concepts and designs of the prior art. Therefore, it can be appreciated that there exists a continuing need for new and improved liquid dispensing air freshener system which can be used for freshening air and/or dispensing pesticides. In this regard, the present invention substantially fulfills this need.

Various objects and advantages of the present invention, and its most novel features, will be particularly pointed out in this disclosure.

OBJECTS AND ADVANTAGES

General Objectives

It is a general object of this invention to provide a device which is able to generate an adjustable fragrance concentration over a relatively long time and which can be refilled by changing a replaceable or disposable cartridge-style container of fragrance-producing liquid or pesticide.

A still further object of the present invention is to provide a device that allows for readily replaceable cartridges which can be quickly inserted into the device for replenishment of the fragrance-enhancing material.

Another object of the present invention is to provide the ability to use more than one fragrance cartridge so that a user can select between fragrances.

Another object of the present invention is to provide a device that can quickly switch from one variety of dispensed fragrance to another with minimal mixing of the fragrances.

Another object of the present invention is to provide a device that can dispense different liquids from different cartridges at the same time and in any combination to create any desired output blend of fragrances.

Another object of the present invention is to provide a device that can dispense different liquids from a single cartridge that contains multiple chambers for different fragrances, and to dispense each liquid individually or in any combination from the cartridge.

Another object of the present invention is to provide a device that is capable of determining the type of liquid that is supplied to it and then has the ability to intelligently use this data to optimize its operation to achieve maximum performance in the vaporization and delivery of the liquid to the ambient air.

Another object of the present invention is to provide a device that has internal and/or external sensors that can measure the ambient conditions, such as temperature and humidity, in order to achieve maximum performance in the vaporization and delivery of the liquid to the ambient air.

A still further object of the present invention is to provide a device that may be retailed at a sufficiently low price as to encourage its widespread use in homes.

Multiple Use Air Freshener

Another object of the present invention is to provide an air freshener which is useable in vehicles, airplanes and buildings or in any other areas where air fresheners would be of benefit, and of which may be transported there between.

Another object of the present invention is to provide an air freshener which can be manufactured as part of a new product, such as manufacturing the device into the dash of a new car.

Another object of the present invention is to provide an air freshener which can be adapted for use with an existing product, such as an existing air-conditioning system.

Another object of the present invention is to provide a device which can be adapted to be used as a wall receptacle plug-in air freshener.

Another object of the present invention is to provide a device which can be used to dispense insect repellant or other liquid types.

Multipurpose Chassis Design

Another object of the present invention is to provide a single, multipurpose chassis that is shaped and sized to allow a single device to be used in many different ways, such as tabletop, under-counter, ceiling vent and heating/cooling duct applications.

Another object of the present invention is to provide for the use of an unlimited number of specialized chassis that are shaped and sized to allow the devices to be used in special configurations, such as automotive cigarette lighter jacks and car dash panels.

Another object of the present invention is to provide a modular chassis so that an unlimited number of fragrance cartridges can be modularly configured together into a single chassis or whereby multiple chassis can be stacked together to function as a single unit.

Another object of the present invention is to provide an extremely compact chassis option for portability so that it can be easily carried around and used anywhere, such as in a car or at an office desk.

Another object of the present invention is to provide a compact chassis in the form of a "plug-in" so that it can simply be plugged directly into a wall power outlet.

Another object of the present invention is to provide an air freshener chassis that can have multiple evaporation chambers, one for each cartridge or fragrance to allow a perfect fragrance output transition from one scent to another with very little mixing of fragrances.

Another object of the present invention is to provide a dual-purpose chassis where a user can access the device's evaporation chamber in order to add other non-cartridge based scent producing materials, such as fresh flowers, potpourri, or perfume whereby the device is used to help disperse the fragrance into the ambient air.

Multiple Methods to Vaporize and Disperse Liquid

Another object of the present invention is to provide the ability for the device to use multiple liquid types, such as highly volatile perfumes and low volatile oils, and then to provide the means to effectively vaporize them and deliver the resulting vapor into the ambient air.

Another object of the present invention is to provide the ability to use multiple methods to enhance the evaporation of its dispensed liquid, such as fans, heated elements or piezo-electric vibrators, and to use any one or all combinations of methods so that virtually any type of liquid can be readily vaporized:

1) The present invention can use a motor-driven fan which actively circulates air around the dispensed liquid to assist in the vaporization of liquid fragrance and to help expel the vapor into the ambient air;
2) The present invention can use a heated reservoir for the dispensed liquid fragrance whereby applied heat can readily accelerate the atomization of liquid as well as provide natural heat convection to convey the fragrance into the ambient air without the need for any moving parts;
3) The present invention can use a piezo-electric vibrator, that converts electrical energy into vibrational mechanical energy, such as ultrasound, that can be used to atomize liquid.

Use of Cartridges

Another object of the present invention is to provide a device whereby a user can quickly and simply swap out any desired fragrance cartridge, thus allowing a user to instantly replenish a spent cartridge or to change the cartridge selection of fragrance for variety.

Another object of the present invention is to provide the ability to use both refillable and disposable cartridges to contain liquid fragrance and/or pesticides.

Another object of the present invention is to provide the ability to use a single, multi-chamber cartridge that can contain a plurality of different fragrances.

Another object of the present invention is to provide the use of a leak-free cartridge system whereby a full or empty cartridge can be removed and reinstalled without any leakage.

Another object of the present invention is to provide a means to convey data from a cartridge about its liquid content to the dispenser's controller, such as a cartridge with an embedded chip that possess data about its contained liquid and electrical terminals that can be used to convey this data from the cartridge to the controller.

Use of Fixed Tanks

Another object of the present invention is to provide a device whereby refillable fixed tanks can be used to store liquid rather than cartridges. Large tanks would enable fewer service intervals for refilling, as would be desirable for commercial use.

Programmable Controller

Another object of the present invention is to use an electronic, programmable controller that has the ability to control all aspects of the liquid dispenser for high performance operation.

Another object of the present invention is to provide a device that is capable of determining the type of liquid that is supplied to it and then has the ability to intelligently use this data to optimize its operation to achieve maximum performance in the vaporization and delivery of the liquid to the ambient air.

Another object of the present invention is to provide the means for an electronic controller to establish communication with an embedded chip that is installed inside a cartridge for the purpose of using the data stored there for precise dispensing and vaporization control of the specific liquid contained inside the cartridge.

Another object of the present invention is to provide the means for an electronic controller to establish communication with a remote control device, for the purpose of allowing remote control of the various features of the liquid dispenser.

Multiple Power Source Capability

Another object of the present invention is to provide the ability to use multiple power sources, such as disposable or rechargeable batteries, regular household AC power, or 12/24 volt DC automotive battery power, including any combination of them.

Another object of the present invention is to provide the ability of its use with an adapter that would allow it to work in a automotive style cigarette lighter power jack.

Another object of the present invention is to provide the ability to use solar-cells to utilize the energy derived from natural sunlight or light emitted from regular room light fixture.

Special Bathroom Air Freshener

Another object of the present invention is to provide an air freshener chassis design for the bathroom so it can be inconspicuous and unobtrusive to maintain look the traditional bathroom.

Another object of the present invention is to provide a modular air freshener chassis that can be mounted onto a standard toilet's water tank and which is shaped to fit and blend in with the tank.

Summary of Objectives

The present invention accomplishes the above-stated objectives, as well as others, as may be determined by a fair reading and interpretation of the entire specification.

SUMMARY OF THE INVENTION

In the view of the foregoing disadvantages inherent in the known types of air fresheners now present in the prior art, the present invention provides an improved liquid dispensing air freshener. As such, the general purpose of the present invention, which will be described subsequently in greater detail, is to provide a new and improved liquid dispensing air freshener and method that has all the advantages of the prior art and none of the disadvantages.

It is the principal objective of the present invention to provide a multipurpose, cartridge-based liquid dispensing air freshener that can be mounted in many chassis variations in order to maximize its utility. The dispensed liquid includes perfumes, air fresheners, household cleaning materials, sanitizers, disinfectants, repellents, insecticides, aroma therapy formulations, medicinal, therapeutic liquids, or other liquids which benefit from vaporization for use.

The basic components of the present invention consists of at least one refillable or disposable cartridge that can contain liquid, at least one liquid pump, at least one liquid reservoir, an electronic controller and a specially designed chassis.

Liquid Cartridge System:

With many previous art devices, it can be inconvenient to replace the air freshener dispenser or replenish the fragrance solution. Some liquid dispensers can be very messy to refill. The present invention addresses these problems by making use of a unique removable liquid cartridge system. The present invention uses a special disposable or refillable cartridge to contain a fragrance emitting liquid. The cartridge is designed to be easily removable from its chassis, so that it can be refilled or disposed of. This cartridge also provides many advantages and options, such as:

1) Convenient Access: The replaceable cartridge can be inserted into a slot at the front of the cabinet. This position allows the user easy reach to service the unit;
2) Convenient Packaging Reduces Mess: The cartridge is a convenient, leak free container for liquids, allowing the user to handle it without coming in contact with the liquid inside, which can be a harsh, extremely concentrated chemical (such as insecticides).
3) Economical Use of Fragrances: A reusable and refillable cartridge options allows a user the ability to purchase fragrances in large quantities, such as economical gallon sized jugs. The cartridge can be simply removed from the cabinet, its cap removed and then refilled with solution;
4) User Choice of Fragrances: A refillable cartridge provides a user the ability to utilize any desired kind of readily available fragrance, such as a favorite perfume;
5) Convenience of Service: An optional disposable cartridge allows the user the convenience of simply discarding a spent cartridge. This relieves the user from the task of refilling the cartridge and from the potential of making a mess. A user has only to pull out and discard a spent cartridge and then simply insert a fresh one into the device;
6) Solution Level Indication: A cartridge made of a transparent or semitransparent material would allow a user to visually see the fluid level inside the cartridge simply by glancing at it, thereby allowing the user to know how much fluid remains in the cartridge. An optional electronic fluid level detector can also be used sense the level of the liquid inside the cartridge and then provide feedback for the user, whereby the controller can flash a lamp and/or signal a beeper to occasionally chirp to indicate a low fluid level condition.

The cartridge contains a unique spring-loaded drain valve that is normally closed to prevent any leakage while the cartridge is removed from the cabinet. This drain valve automatically opens once the cartridge is inserted into the air freshener chassis and closes once the cartridge is removed. This special valve system keeps the cartridge from leaking and thus allows a user to remove it at any time, even if the cartridge is completely full, without leakage. This feature also allows a user to swap out different cartridges for different fragrances, if so desired.

The cartridges can also be made so that a hollow needle can pierce the cartridge's skin to tap into the cartridge's liquid supply. Liquid will be dispensed through the hollow needle into the liquid pump. The cartridge material can be made from a resilient material such that the needle's insertion point can be self healing, so that it will not leak if the needle is removed from the cartridge.

The cartridge is designed to use an optional embedded chip that possesses data about the cartridge's liquid type for high performance purposes. Electrical terminals on the cartridge mate with contacts inside the liquid dispenser to convey this data from the cartridge to the liquid dispenser's controller. This data can also be used by the controller to determine how much liquid to dispense, when to dispense it and to more precisely vaporize the liquid. For example:

1) If a cartridge contains a scented oil that has low volatility, the controller can calculate the use of a higher reservoir heater setting and a higher fan speed to achieve a desired fragrance output concentration;
2) The dispenser can be programmed to use "rate of vaporization" data that is downloaded from the cartridge together with the liquid dispenser's sensors that measure the ambient conditions to ensure that the liquid has time to vaporize before dispensing more liquid. For example, if the data from the cartridge describes a liquid that is highly concentrated and volatile, the liquid dispenser can then dispense a smaller amount of the liquid at one time. After a calculated time lapse, the controller can then dispense more liquid;

The data about the cartridge's contents can also be used for display purposes. For example, if a cartridge is called "Rose Garden," this name data can be stored in the embedded chip and downloaded to the dispenser's alphanumeric display system. This feature would work very well for remote controls.

The cartridge can also use a mechanical means to store cartridge data that can be conveyed to the controller (which can save costs). For example, the cartridge can contain a key type system where physical key ridges on the cartridge can mate with a receiving edge in the dispenser that can contain either mechanical or solid state switches to record the key's values. For instance, if the system allows for the liquid to be characterized by 16 variable states, a protruding edge on the cartridge can have 4 notches of which 16 different positions can be derived.

The cartridge can also be made to use internal bladders, whereby the cartridge would exist as a shell to encase and protect the liquid filled bladder and provide a modular structure for docking Bladders can provide several benefits:

1) As the volume of liquid is drawn out of the cartridge, air must be allowed to enter to displace the liquid (otherwise the cartridge would be crushed). Therefore a pressure relief valve is used to let air in. The use of a bladder would allow the cartridge shell to simply use ventilation holes, where air can freely circulate around the bladder as the bladder's volume is consumed;
2) For a special liquid mixture, it may be desired to isolate it from the ambient air until the time that it is dispensed (for example: sterile, hermetically sealed medicinal solution). A regular pressure relief valve would simply let atmospheric air into the cartridge, where it would be in contact with the liquid. Bladders can be made to be sealed and hold only liquid and no air;
3) Bladders would also work well in situations where the dispenser is used in inverted positions. A bladder would allow a constant flow of liquid regardless of the direction of gravity.

Multiple Liquid Cartridge System:

Many previous art devices emit only a single fragrance. A device that can emit more than one fragrance can provide for a pleasing variety. The present invention is designed to release an unlimited number of different fragrances by using multiple liquid cartridges or multiple-chamber cartridges. The liquid dispensing unit can be programmed to dispense liquid from any of the installed cartridges in any desired combination and interval.

Liquid Tank System:

One embodiment of the present invention is to accommodate the use of non-cartridge, tank style containers. A much larger tank would allow the ability for the device to hold a vast amount of liquid, which would provide a user the convenience of less frequent service refill intervals.

Liquid Pump:

The present invention uses a liquid pump assembly that is designed to pump liquid from a cartridge or liquid holding tank into an evaporation chamber. The pump assembly components couple with a cartridge once the cartridge is inserted into the air freshener chassis. The pump assembly contains an inlet orifice that automatically pushes open the cartridge's drain valve so that liquid can flow into the pump assembly. An electric pump can be energized to dispense a precise amount of fluid from the cartridge to an evaporation chamber. This liquid pump can also be used with fixed tank systems as well, instead of the cartridge.

Evaporation Chamber:

The present invention uses an evaporation chamber to vaporize any liquid that is conveyed into it. This well ventilated evaporation chamber consists of a liquid fragrance reservoir that provides a place to store liquid after it has been pumped from the cartridge. A material such as a wire mesh or sponge can be employed in the reservoir to accept and confine the dispensed liquid while time lapses during the vaporization process. This porous material has a large surface area that facilitates the evaporation of the liquid into the ambient air.

While normal evaporation of the liquid can work well with some of the present invention's chassis variations, this evaporation chamber can utilize any assisted method to help vaporize the liquid fragrance and disperse it into the ambient air, such as fans, a heated elements or piezo-electric vibrator s or any combination thereof:

1) Fan: A fan creates an airflow through the evaporation chamber, which assists the liquid to vaporize much faster and propels the fragrance from the reservoir to the ambient air. The fan can be a variable speed device so that it can operate at any desired level. A very low speed can be used for quiet, low power and mild fragrance emission. A high speed setting can be used to maximize the air freshener's output;
2) Heated Element: A heated element positioned below the reservoir can provide heat to the liquid to help vaporize it much faster. Natural convection from this heated element will help propel the fragrance to the ambient air. A fan can also be used with this heated element to provide maximum performance;
3) Piezoelectric Vibrator: A piezoelectric vibrator can also be used in the evaporation chamber. This electromechanical transducer essentially helps to atomize the fragrance in the form of fine particles or droplets.

Electronic Programmable Controller:

The present invention employs a programmable electronic device that is designed to control all of the dispenser's various features and can allow a user to select from a wide variety of pre-programmed liquid dispensing sequences. It can also be programmed for customized operation. The electronic programmable controller has the capability to:

1) Automatically power itself on and off as required;
2) Provide dispensing control over any installed liquid pumps to vary the liquid output volume, duration and frequency in order to provide any desired liquid output;
3) Automatically power an installed fan with the ability to vary its speed and consequential air throughput in very fine increments that can coincide with a calculated liquid output and vaporization rate that is optimal for the type of liquid that is being dispensed;
4) Select and control the output of liquid from a plurality of installed cartridges and/or from multi-chambered cartridges as well as from fixed tanks;
5) Select and program various operational timed intervals, such as the sequence and timing for output from any installed cartridge and daily power on/off cycles;
6) Indicate which cartridge is currently selected and/or operating in a multi-cartridge system;
7) Communicate with an embedded chip that is installed inside a cartridge for the purpose of using the data stored there to determine the type of liquid that is supplied and then intelligently use this data to optimize its operation to achieve maximum performance in the precise dispensing, vaporization and delivery of the liquid into the ambient air. This would provide the ability for the device to more efficiently use multiple liquid types, such as highly volatile perfumes and low volatile oils;
8) Switch the electrical polarity of an installed fan to reverse the flow of air whereby the fragranced air can be emitted behind the chassis where special ductwork can be attached to receive and discharge the fragrance to a depository;
9) Detect the fluid levels inside each installed cartridge and provide output indication of their fluid levels in various forms, such as a panel display or lamp;
10) Alert a user of a low fluid level such as visually illuminating and/or flashing a lamp or audibly chirping a beeper;
11) Display the type of fragrance that is contained within an installed cartridge;
12) Use an external switch and/or communicate with an external device to convey operational information to/from the dispenser such as: room occupancy from an external motion sensor or external equipment status, such as the startup and shutdown of an air conditioning system;

13) Monitor internal and external sensors to provide the dispenser with ambient conditions such as temperature and humidity so that this data can be processed to provide optimal performance;
14) Allow for periodic or continuous fragrance dispensing;
15) Dispense different liquids from different cartridges at the same time in any combination to create any desired output blend of the fragrances;
16) Communicate with a wired or wireless remote control device for the purpose of allowing the remote control to control the various features of the present invention.

The controller can use a display system that can allow a user better interface with the controller and can provide output data concerning the operation and performance of the device. For instance, if a cartridge is inserted into the device that is called "Spring Rose" for its rose scented fragrance, the controller download this information from the cartridge and display this name on an alphanumeric panel. Programming options for this particular cartridge can also be displayed.

Chassis Embodiments:

The present invention can be housed in many types of special chassis embodiments to allow the device to be used in a wide range of applications. Some of these chassis embodiments are listed here:

1) Modular Chassis: A modular chassis allows the present invention to expand in two ways:
   a) Separate independent chassis' can be modularly stacked and connected together to function as a single unit. For example, two "five-cartridge" liquid dispensers can be stacked together to then provide a ten-cartridge system.
   b) Modular subsections can be assembled onto a main controller body element. The modular subsections are designed to be simply snapped onto each other and then onto a controller body to form a single functioning unit, whereby an unlimited number of subsections can be added;
2) Dual-Purpose Chassis: The present invention can use a chassis design that provides for a dual-purpose evaporation chamber. Not only does this dual-purpose evaporation chamber have a liquid reservoir that can accept and vaporize liquid from fragrance cartridges, the chamber can also be accessed by a user for the insertion of scented objects. The fragrance from these objects can be propelled into the ambient air by the device's fan. Examples of some fragrant objects include fresh flowers, potpourri, bars of soap and perfume.
3) Multi-Function Chassis: The present invention can include chassis elements that allow its use in a wide variety of applications. For instance, mounting brackets can be added so that the chassis can be easily bolted onto an air conditioning duct so that fragrance can be discharged directly into the ductwork for distribution throughout a building. For another example, a duct (such as a 90 degree elbow) can be attached to the chassis so that the fragrance output can be directed down through an office building's ceiling panel, or ducted through a vent into a restroom.
4) Compact Wall "Plug-In" Chassis: The present invention can be constructed in a compact chassis with a built-in electrical plug so that it can function as a wall receptacle plug-in. This multi-fragrance plug-in can then be used virtually anywhere in the house or office building.
5) Micro Chassis: A micro-sized chassis embodiment of the present invention provides for portability. This very small air freshener can then be easily carried in a pocket or purse to be used anywhere, such as in the car or at an office desk. This tiny chassis also allows the device to be used in novel ways, such as using it in a motor vehicle's cigarette lighter power socket.
6) Vehicle Dash Panel Chassis: The use of perfume dispensing devices in the car is a fact that is known by everybody, with the object of creating more pleasant ambient conditions for the driver. This is due to the that unpleasant odors frequently permeate the interior of the vehicle, which emanate either from the exhaust gases or from the exterior. All this is further aggravated in the case of vehicles used by smokers in which the smell of tobacco lingers inside the car even days after the vehicle has been used. The present invention allows for a specially constructed chassis to optimize its use in motor vehicles. This compact chassis can be adaptable to fit directly into the dashboard of any motor vehicle, where it can be powered by the vehicle's electrical system and positioned to be within easy reach of the driver. This air freshener system can be added to the vehicle as an aftermarket device or as an original equipment from the vehicle's manufacturer. The air freshener can discharge fragrance directly into the vehicle and/or into the vehicle's air conditioning ductwork
7) Vehicle Stereo-Sized Chassis: Yet another adaptation of the present invention's chassis is to allow it to be installed into a motor vehicle's stereo panel as an aftermarket device. As most vehicles are provided with industry standard stereo panels, the present invention can make use of this area to mount an air freshener. A specially designed chassis that is sized just like a stereo system can simply be slipped into the dash panel. This chassis design can also be used wherever a standard car stereo system is used.
8) Toilet Tank Mounted Chassis: Air fresheners are very frequently used in bathrooms. One embodiment of the present invention is designed to take advantage of the unused space that exists above the average toilet water tank for a storage location for an air freshener. This embodiment uses a chassis assembly that consists of a unique modular cabinet housing that is designed to mount onto the top rim of a standard toilet water tank, inserted between the water tank and the water tank's lid. It is shaped to blend in with the design of the water tank for aesthetics. The bottom of the cabinet has guides that allow the cabinet to fit onto the water tank without the need for fasteners. The top edge of the cabinet housing is a rim just like that of the water tank to allow the original toilet's lid to be re-installed. This allows the stock toilet lid to be reused so that the general design of the toilet can be maintained and to help the cabinet to blend into the existing bathroom décor. The cabinet can have its own custom top as well. The general design of the cabinet is modular in nature so that a maximum of utility can be achieved. This modular design allows other modular cabinets housing assemblies to be installed above or below it.

One important object of the present invention is to provide the most inconspicuous and unobtrusive cabinet as to maintain look the traditional bathroom. The present invention achieves this because the toilet water tank mounted modular cabinet is shaped like the water tank so as to blend in with the existing facility, making it inconspicuous. The aesthetics of the toilet then appear normal, with the appearance of only a slightly taller than usual water tank. The modular cabinet can be provided with its own detachable lid, but reusing the original stock toilet lid will better preserve the original toilet aesthetics.

For universal applications, this modular cabinet can be offered in a generic cabinet shape or "skin" that is designed to work and look good with a wide range of brands and models of toilets. Adjustable mounting guides can assure a secure fit with a wide variety of tank shapes. This will enhance the present invention's ability to be used on large numbers of existing toilets.

The modular cabinet's position on the water tank also allows easy installation of the device as it merely sits on the tank, requiring no fasteners. Guides on the cabinet's bottom mates with the water tank's rim to keep the cabinet securely in place. The top of the modular cabinet has a rim just like the water tank so that the original lid can be attached to it. This modular design also allows it to be easily removed so that quick service to the components inside the water tank can be made such as freeing up a stuck flush valve.

Internal and External Sensors:

The present invention has the capability of communicating with a variety of optional internal and/or external sensors, switches or other devices to provide the controller programming and/or feedback for optimal performance. For instance, an external motion sensor can be used as an input to provide room occupancy signals. This occupancy data would allow the device to deviate from its normal programming for better efficiency. For example, if the device is normally programmed to emit fragrance in a public restroom during normal business hours, the device can deactivate if it detects no traffic, such as when the building might be closed for a holiday. Likewise, the unit can be activated if enough traffic is detected on a weekend or after business hours.

Internal and/or external sensors can also be used to measure the ambient conditions, such as temperature and humidity. This allows feedback for the electronic controller in order to achieve maximum performance for the vaporization and delivery of a liquid into the ambient air.

An optional sensor can also be used in the reservoir tray to monitor the liquid level to prevent an overflow, in which case the dispenser can be programmed to wait until enough liquid has vaporized before dispensing more liquid.

Power Supplies:

The present invention is designed to use any type of available power source in order to maximize its usefulness for any circumstance. For some examples:

1) AC/DC Power: The device can use both AC and DC power sources. Replaceable or rechargeable batteries can power the device for the situation where an AC source is unavailable. When available, an AC source can be used to power the device as well as charge the batteries;
2) Solar Panel: The device can use a solar panel to provide power, which would be of great benefit for a portable, micro-sized chassis that is used in a car. The solar panel can also be used to charge an optional battery;
2) Vehicle 12 Volt Power Jack: The device can use an adaptor so that it can tap into an automotive 12 volt power system through a standard plug-in power jack. This would allow the device plenty of power without the need for internal batteries or a solar panel.

Insecticides and Other Uses:

The present invention can be used for virtually any situation what requires the vaporization of a liquid. The dispensed liquid includes perfumes, air fresheners, household cleaning materials, sanitizers, disinfectants, repellents, insecticides, aroma therapy formulations, medicinal, therapeutic liquids, or other liquids which benefit from vaporization for use.

Summary:

Although only a few embodiments of the present invention have been described, it should be understood that the present invention may be embodied in many other specific forms without departing from the spirit or the scope of the present invention. The present examples are to be considered as illustrative and not restrictive, and the invention is not to be limited to the details given herein, but may be modified within the scope of the appended claims along with their full scope of equivalents.

The above mentioned objectives and advantages of this invention and the manner of attaining them will become more apparent and the invention itself will be best understood by reference to the following detailed descriptions of the invention taken in conjunction with the accompanying drawings.

BRIEF DESCRIPTION OF THE DRAWINGS

Various other objects, advantages, and features of the invention will become more readily apparent to those skilled in the art from the following detailed description when read in conjunction with the accompanying drawings, in which:

FIG. 29 is a front perspective view of a liquid cartridge and liquid pump assembly to show how they would normally be mated together inside the cabinet.

FIG. 30 is a rear perspective view of a liquid cartridge and liquid pump assembly to show how they would normally be mated together inside the cabinet.

FIG. 31 is a lower rear perspective view of a liquid cartridge and liquid pump assembly with the liquid pump assembly slightly cocked from the normal alignment with the cartridge to illustrate the orientation of the mating orifices that communicate the liquid from the cartridge to the pump assembly. This view also shows the liquid level sensor on the pump assembly and its mating window pane on the cartridge.

FIG. 35 is a top view of the present invention that uses a portable, a micro-sized chassis.

FIG. 36 is a side view of the present invention that uses a portable, a micro-sized chassis.

FIG. 37 is a front view of the present invention that uses a portable, a micro-sized chassis.

FIG. 38 is a rear view of the present invention that uses a portable, a micro-sized chassis.

FIG. 47 is a rear perspective view of an embodiment of the present invention where a specially designed compact, micro-chassis is shaped to work as a wall receptacle plug-in.

FIG. 50 a front view of an embodiment of the present invention where a specially designed compact, micro-chassis is shaped to work as a wall receptacle plug-in.

REFERENCE NUMERALS

Figure 1:
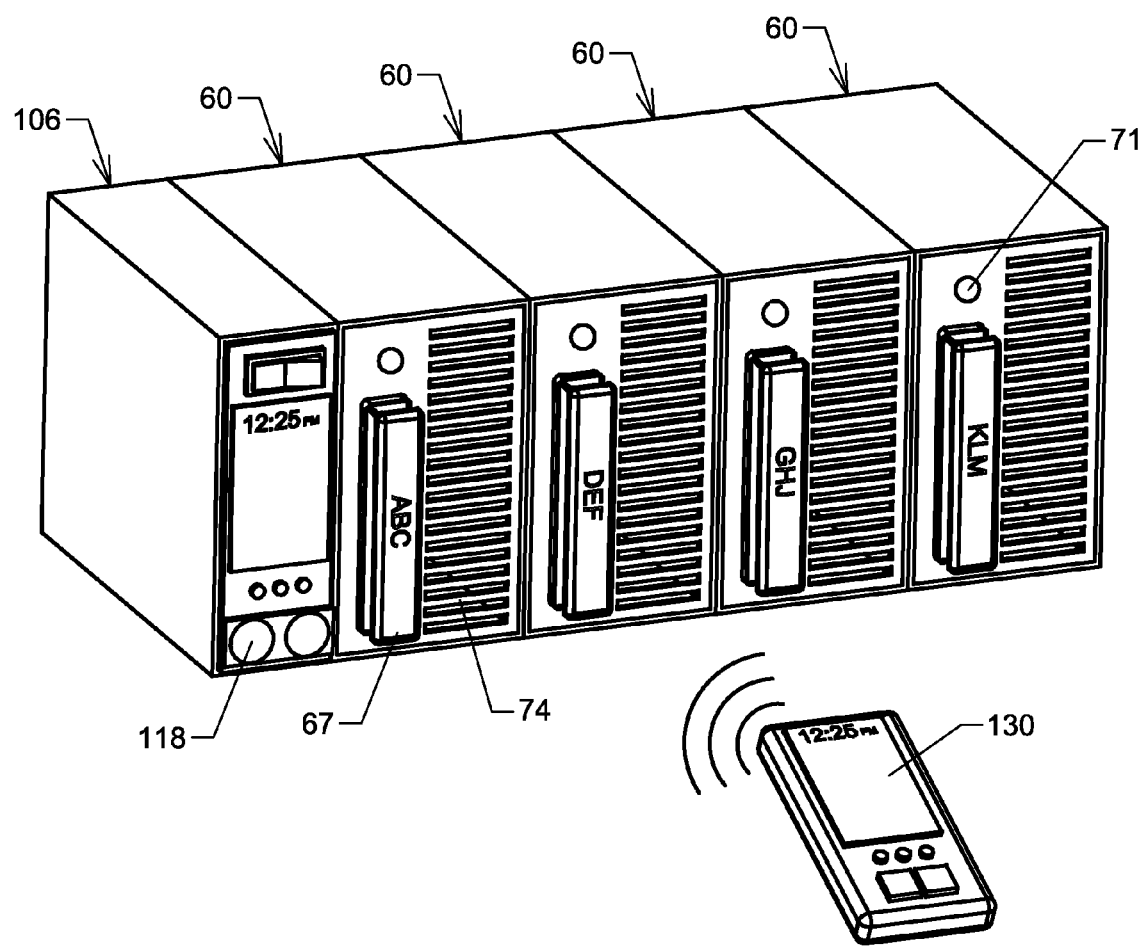
FIG. 1 is a front perspective view of a modular embodiment of the present invention, where an unlimited number of modules can be assembled together to form a single unit. Four modules are shown assembled onto an electronic controller to complete an air freshener assembly. A remote control is shown as an alternate means to remotely control the device.

60 Assembly, Modular Liquid Dispenser
61 Assembly, Modular Toilet Liquid Dispensing
62 Assembly, Micro Liquid Dispenser
63 Assembly, Wall Cartridge-based Liquid Dispenser
64 Assembly, Electronic Controller
65 Assembly, Liquid Pump & Cartridge Mounting Sleeve
66 Fan
67 Cartridge, Disposable Liquid Fragrance
68 Cartridge, Refillable Liquid Fragrance
69 Cap, Cartridge Refill
70 Label, Cartridge
71 Switch, Lighted
72 Button, Control
73 Cover, Liquid Dispenser Assembly
74 Grill, Fragrance Outlet
75 Grill, Air Inlet
76 Chamber, Fragrance Evaporation
77 Cover, Battery
78 Tray, Battery
79 Battery
80 Receptacle, Power
81 Plug, Electrical
82 Coupling, Duct
83 Duct, Exhaust
84 Duct, Air Inlet
85 Basket
86 Tube, Liquid Transfer
87 Pump, Liquid
88 Sensor, Liquid Level
89 Window, Liquid Level
90 Drain, Cartridge
91 Valve, Drain
92 Seal, O-Ring
93 Orifice, Pump Inlet
94 Actuator, Valve
95 Compartment, Cartridge
96 Vent, Pressure Release
97 Panel, Solar
98 Slot, Cartridge Mounting
99 Panel, Switch Programming
100 Light, Night
101 Reservoir
102 Tank, Toilet Water
103 Guide, Mounting
104 Tank, Fixed—Refillable
105 Tray, Fragrance Evaporation Reservoir
106 Assembly, Modular Controller
107 Pin, Mounting
108 Cartridge, Multi-Compartment—Single Drain
109 Cord, Hanging
110 Cartridge, Multi-Compartment and Multi-Drain
111 Shoe, Mounting
112 Adapter, Cigarette Lighter Power
113 Mount, Eyelet
114 Joint, Hinged Cigarette Lighter Power Adapter
115 Duct, Air Conditioning
116 Panel, Car Dash
117 Terminals, External Switch Input
118 Sensor, Occupancy
119 Contact, Cartridge Electrical Data Path
120 U.S. Penny
121 Sleeve, Stereo Style Mounting (DIN)
122 Assembly, Car Air Freshener Stereo Replacement Chassis
123 Assembly, Car Dash Internally Mounted Chassis
124 Baffle
125 Assembly, Liquid Pump
126 Assembly, Liquid Dispenser
127 Aperture
128 Guide, Cartridge Alignment and Support
129 Lid, Water Tank
130 Control, Wireless Remote
131 Fitting, Liquid Tube

DETAILED DESCRIPTION OF THE DRAWINGS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Various other objects, advantages, and features of the invention will become more readily apparent to those skilled in the art from the following detailed description when read in conjunction with the accompanying drawings, in which like reference numerals designate like parts throughout the figures thereof.

Modular Liquid Dispensing Air Freshener:

FIGS. 1-6 illustrate the modular nature of the present invention, where an unlimited number of cartridge-based liquid dispensing modules can be assembled together to form a single unit. This unique design allows only one or any combination of installed dispensers to be activated.

FIG. 1 is a front perspective view of a modular embodiment of the present invention, where four modular liquid dispenser assemblies 60 are shown assembled onto a modular controller assembly 106 to complete a single modular air freshener unit. Each modular liquid dispenser assembly 60 has its own fragrance outlet grill 74, liquid fragrance cartridge 67 and a lighted switch 71. A lighted switch 71 allows a user to select (or deselect) the assembly 60 for operation and illuminates to indicate its operational status.

FIG. 1 also illustrates wireless remote control 130 that can be used with the present invention in order to remotely control the device. A wired remote control can also be used. This feature allows the present invention to be mounted in remote places, such as in a ceiling or air conditioner closet, yet allow a user to have a more convenient location for a controller. For example, if the present invention is mounted onto an air conditioner duct, a dual-purpose remote control can program and control both the air conditioner and the liquid dispensing air freshener. The remote control 130 can be equipped with a digital display for easy programming and for device status.

The controller assembly 106 is also capable of determining the type of liquid that is supplied to it and then has the ability to intelligently use this data to optimize its operation to achieve maximum performance in the vaporization and delivery of the liquid to the ambient air. Thus, the cartridges 67 are designed to contain an element that describes the contents of its cartridge, such as data that is programmed into an embedded chip. The controller assembly 106 is designed to establish communication with this embedded chip in an installed cartridge and convey this data to the controller for the precise dispensing and vaporization control of the specific liquid contained inside the cartridge.

Figure 2:
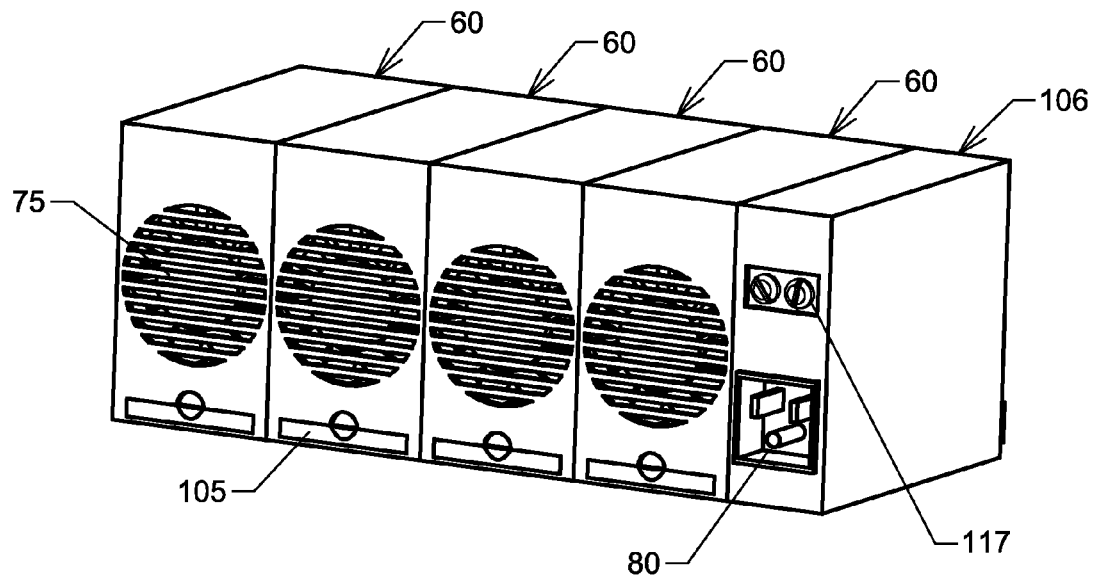
FIG. 2 is a rear perspective view of a modular embodiment of the present invention, where an unlimited number of modules can be assembled together to form a single unit. Four modules that are shown assembled onto an electronic controller to complete an air freshener assembly. This embodiment uses individual fans that are mounted inside each modular liquid dispenser.

FIG. 2 is a rear perspective view of a modular embodiment of the present invention, where four modular liquid dispenser assemblies 60 are shown assembled onto a modular controller assembly 106 to complete a single unit. Each modular liquid dispenser assembly 60 has its own fan and air inlet grill 75, and a fragrance reservoir tray 105.

Power is supplied to the unit by plugging a standard electrical cord into the power receptacle 80. Remote switch input terminals 117 can be used to provide feedback to the liquid dispenser for such things as remote occupancy detectors or control signals from an air conditioning system.

Figure 3:
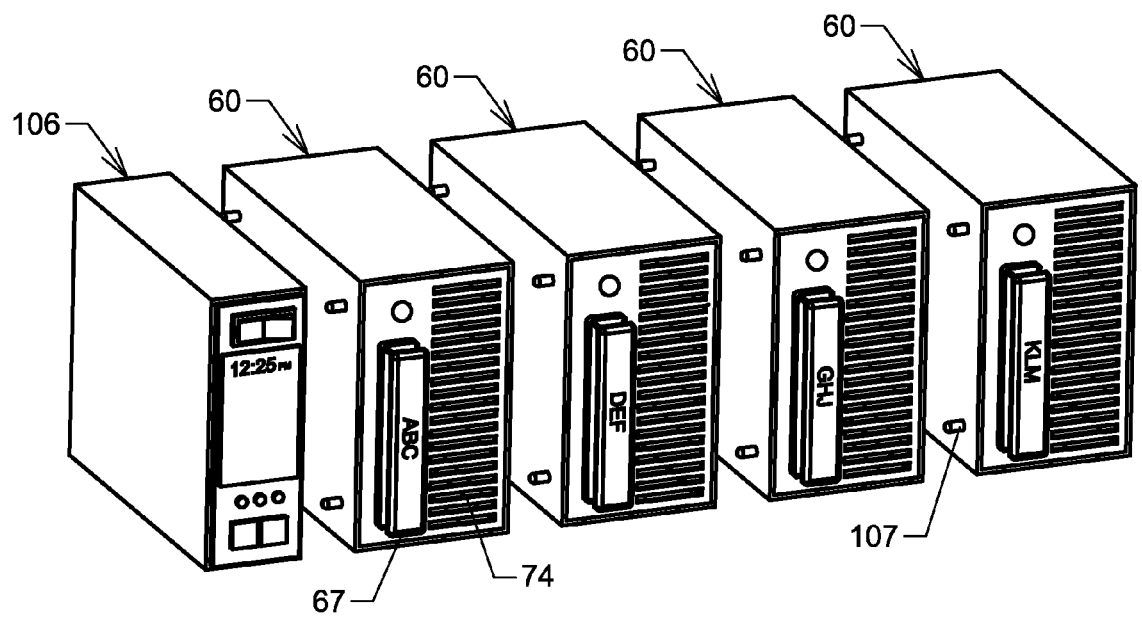
FIG. 3 illustrates how each air freshener module can be assembled onto the electronic controller assembly.

FIG. 3 illustrates how numerous modular liquid dispenser assemblies 60 can be assembled onto a modular controller assembly 106. The mounting pins 107 double function as electrical connectors to provide each assembly 60 with power and programming data from the modular controller assembly 106.

Figure 4:
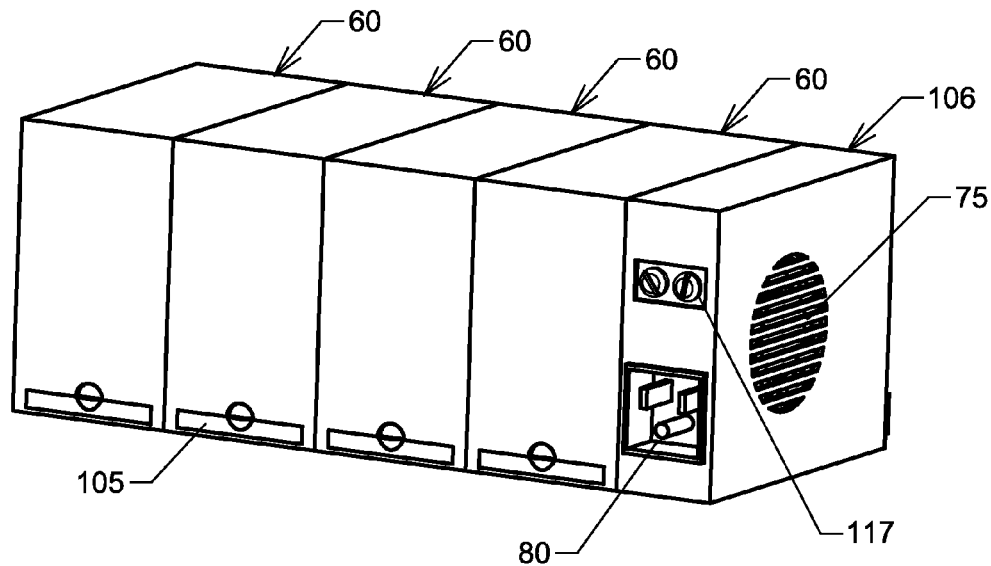
FIG. 4 is a rear perspective view of a modular embodiment of the present invention, where an unlimited number of modules can be assembled together to form a single unit. Four modules are shown assembled onto an electronic controller to complete an air freshener assembly. This embodiment uses a single fan that is mounted inside the modular controller.

FIG. 4 is a rear perspective view of a modular embodiment of the present invention, where four modular liquid dispenser assemblies 60 are shown assembled onto a modular controller assembly 106 to complete a single unit. This embodiment uses a single fan that is mounted inside the modular controller assembly 106 to circulate air from an air let 75 into each dispenser assembly 60.

Figure 5:
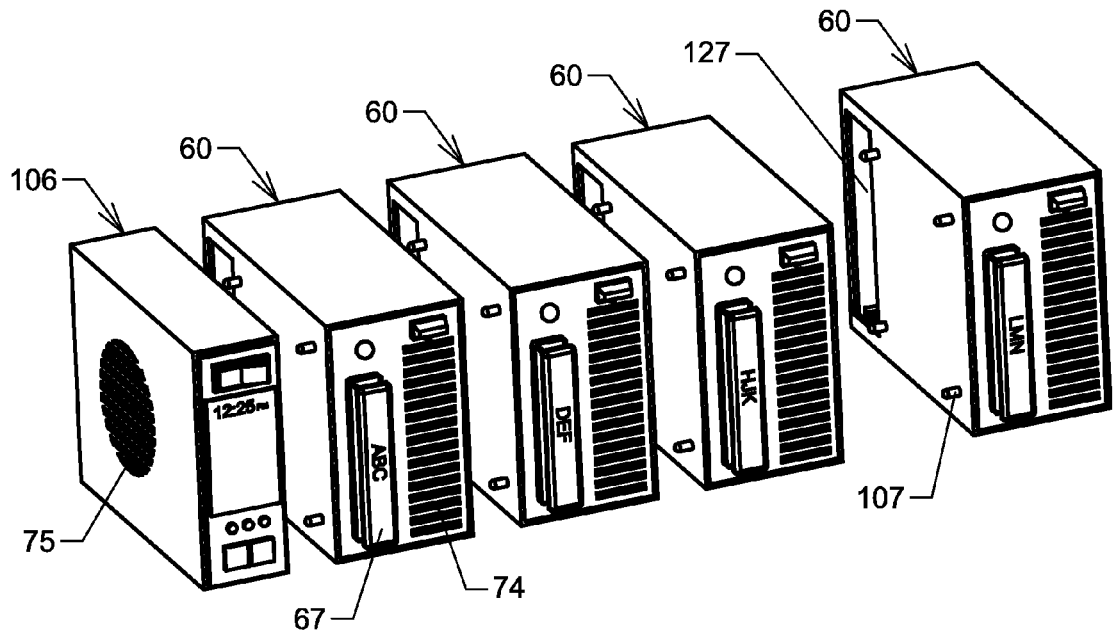
FIG. 5 illustrates how each air freshener module can be assembled onto the modular electronic controller assembly. An aperture in each module creates a ductwork through the completed assembly to allow the use of a single fan that is mounted inside the modular controller.

FIG. 5 illustrates how numerous modular liquid dispenser assemblies 60 can be assembled onto a modular controller assembly 106. This embodiment uses a single fan that is mounted inside the modular controller assembly 106 to draw air in from an air let 75 and propel the air through each dispenser assembly 60 through their apertures 127 and exhaust from the fragrance outlet grills 74. The mounting pins 107 double function as electrical connectors to provide each assembly 60 with power and programming data from the modular controller assembly 106.

Figure 6:
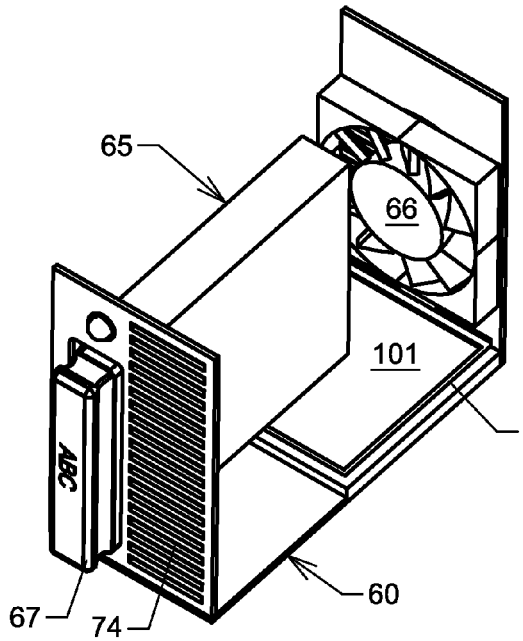
FIG. 6 is a front perspective view of a single air freshener module with its top cover removed to reveal the components inside. This module uses an integral fan.
Figure 7:
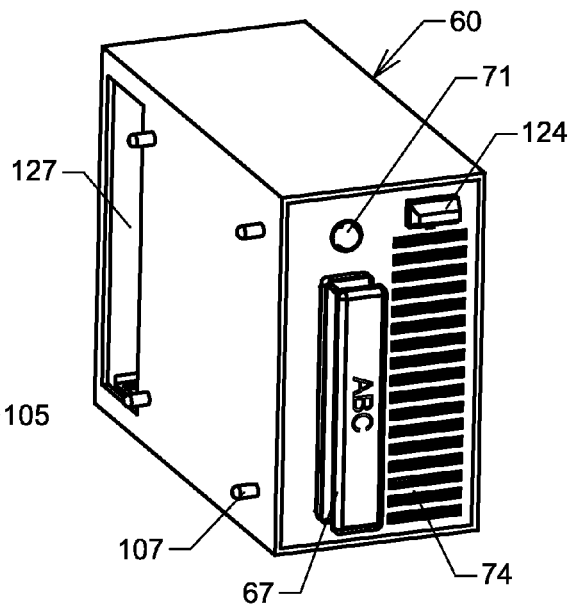
FIG. 7 is a front perspective view of a single air freshener module with an installed cartridge.

FIG. 6 is a front perspective view of a single modular liquid dispenser assembly 60 with its top cover removed to reveal the components inside. This embodiment of the liquid dispenser assembly 60 has its own dedicated fan 66. The liquid pump and cartridge mounting sleeve assembly 65 dispenses a liquid fragrance from a cartridge 67 and deposits it to a reservoir 101. The fan 66 pulls air into the assembly 60 which passes over the reservoir 101 to vaporize and deliver fragrance out of the assembly 60 through a fragrance outlet grill 74. The reservoir 101 is mounted into a reservoir tray 105 so that it can be withdrawn from the assembly 60 for cleaning FIG. 7 is a front perspective view of a single modular liquid dispenser assembly 60 with an installed fragrance cartridge 67. This embodiment of the liquid dispenser assembly 60 has an aperture 127 to allow airflow into the device. The mounting pins 107 double function as electrical connectors to provide each assembly 60 with power and programming data. A lighted switch 71 allows a user to select (or deselect) the assembly 60 for operation and illuminates to indicate its operational status. An optional baffle 124 can be used to restrict airflow through an assembly 106 to prevent undesired mixing of different fragrances from other dispenser assemblies 106.

Figure 8:
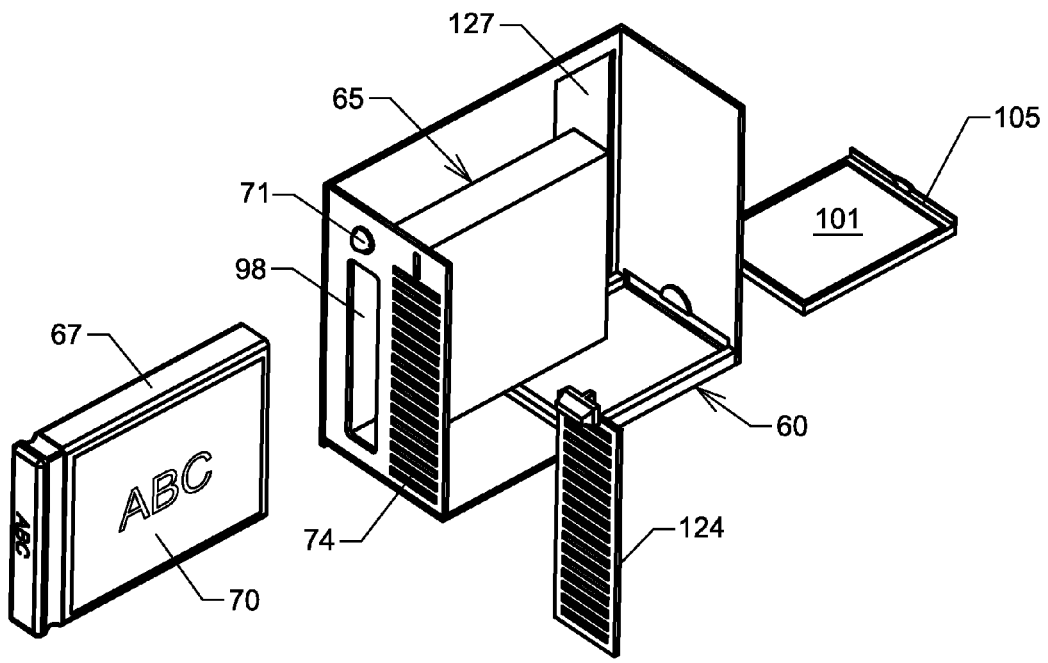
FIG. 8 is an exploded view of an air freshener module to show its parts. This module does not use an integral fan for airflow. It receives airflow through an aperture which will become part of a ductwork once all the modules are assembled onto the fan equipped controller module. A manually operated baffle is shown that would allow the module's output to be reduced, if desired to reduce fragrance mixing between modules. An embodiment of this idea would include electrically operated baffles.

FIG. 8 is an exploded view of a single modular liquid dispenser assembly 60 to show its parts. This embodiment of the liquid dispenser assembly 60 has an aperture 127 to allow airflow into the device. The liquid pump and cartridge mounting sleeve assembly 65 dispenses a liquid fragrance from a cartridge 67 and deposits it to a reservoir 101. Air enters the assembly 60 through an aperture 127 which passes over the reservoir 101 to vaporize and deliver fragrance out of the assembly 60 through a fragrance outlet grill 74. The reservoir 101 is mounted into a reservoir tray 105 so that it can be withdrawn from the assembly 60 for cleaning An optional baffle 124 can be used to restrict airflow through an assembly 60 to prevent undesired mixing of different fragrances from other dispenser assemblies 60. An embodiment of this mechanical baffle 124 idea would involve electrically operated baffles.

Liquid Dispensing Air Freshener:

FIGS. 9-20 illustrate the present invention's liquid dispensing system that is mounted into a single chassis that can accommodate multiple cartridges.

Figure 9:
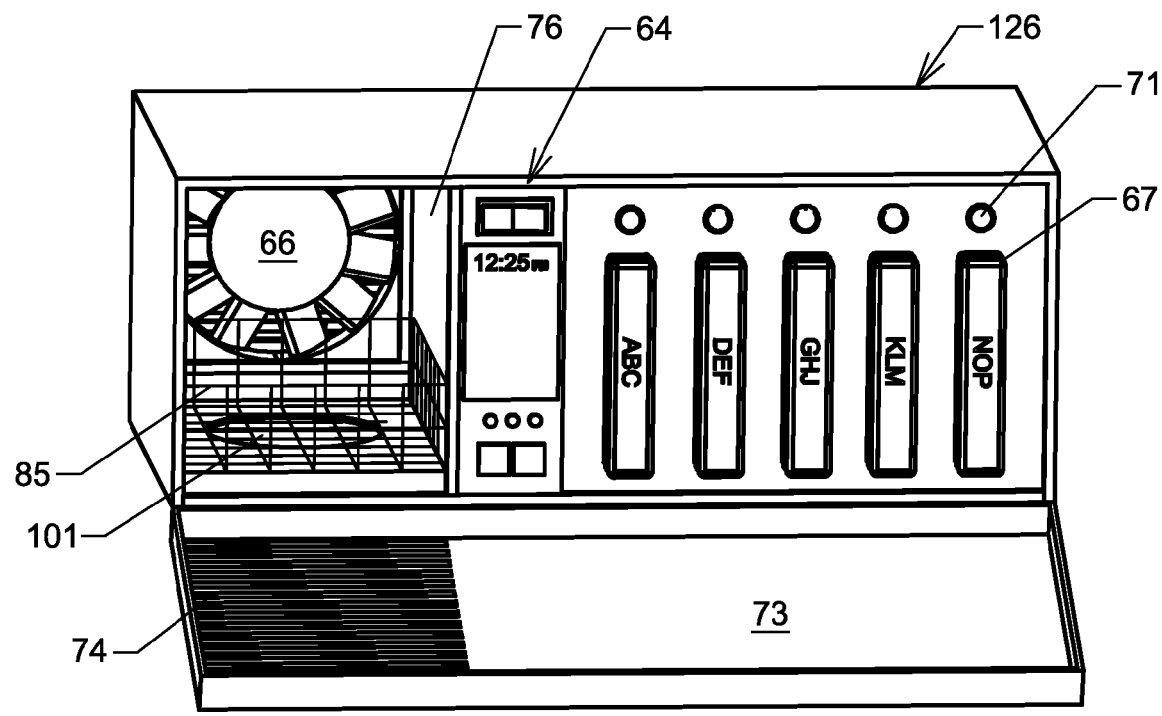
FIG. 9 is a front perspective view of an embodiment of the present invention where one chassis is designed to house numerous cartridges that share a single, dual-purpose evaporation chamber. This view shows the invention with its cover hinged open to reveal five installed fragrance cartridges.

FIG. 9 is a front perspective view of an embodiment of the liquid dispenser assembly 126 where a single chassis is designed to house numerous fragrance cartridges 67 that share a single, dual-purpose evaporation chamber 76. The dual-purpose evaporation chamber 76 not only functions to evaporate liquid fragrance that is dispensed from the cartridges 67 into its reservoir 101 but can also be used to accept any fragrance producing material that can be placed into the basket 85 such as fresh flowers, potpourri, or perfume whereby the liquid dispenser system is then used to help disperse the fragrance into the ambient air. This view shows the invention with its cover 73 hinged open to reveal several installed fragrance cartridges 67. The electronic controller assembly 64 can be programmed to dispense liquid fragrance from any one or combination of any installed cartridges 67. The liquid fragrance is dispensed into a reservoir 101 in the evaporation chamber 76 where a fan 66 evaporates the liquid fragrance and exhausts it through outlet grill 74 into the ambient air. A lighted switch 71 allows a user to select (or deselect) the assembly 126 for operation and illuminates to indicate its operational status.

Figure 10:
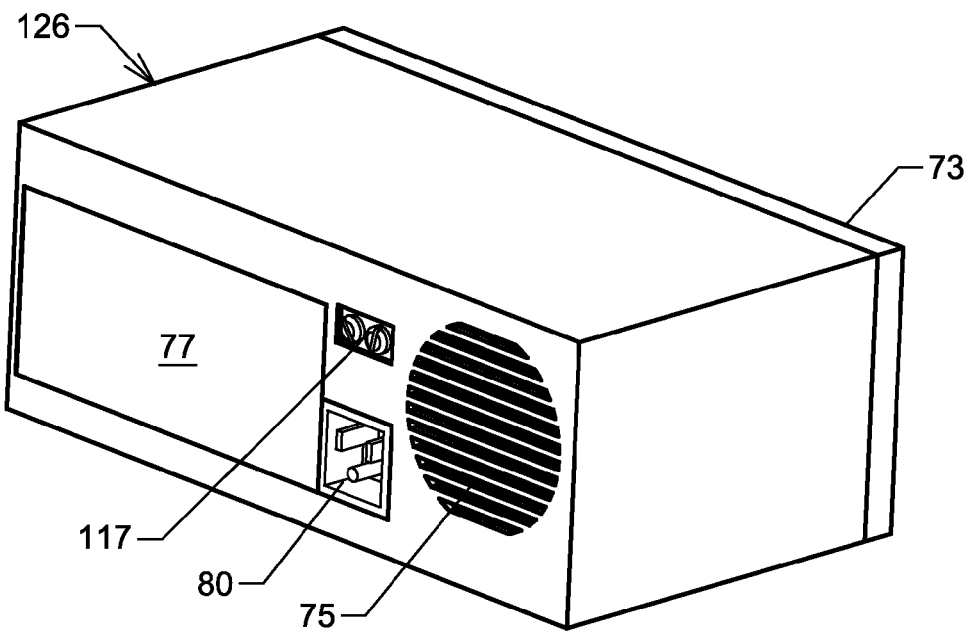
FIG. 10 is a rear perspective view of FIG. 9 to reveal a battery compartment door, power receptacle, external switch input terminals and fan intake grill.

FIG. 10 is a rear perspective view of an embodiment of the liquid dispenser assembly 126 where a single chassis is designed to house numerous fragrance cartridges. This view reveals a battery compartment door 77, power receptacle 80 and air inlet grill 75. This dispenser assembly 126 offers dual power capability of electricity or batteries.

Figure 11:
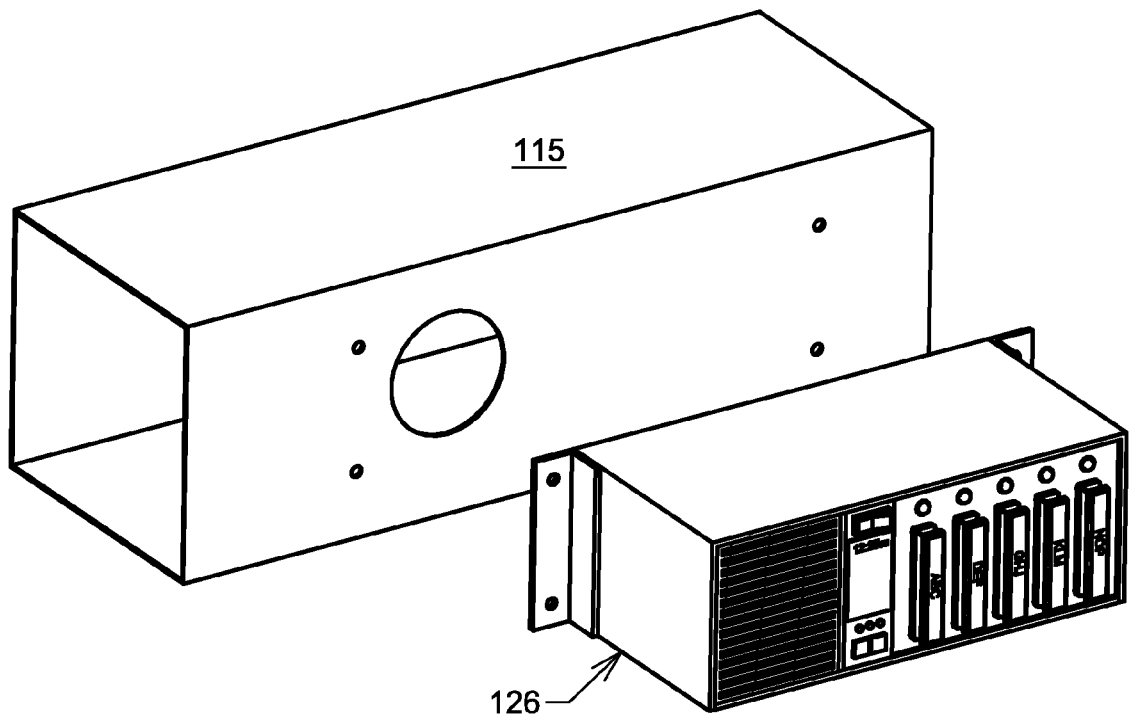
FIG. 11 illustrates how the present invention can be adapted to fit an air conditioning duct.

FIG. 11 illustrates how the present invention can be adapted to fit an air conditioning duct 115. Remote switch terminals 117 (shown in FIG. 12) can be used to allow the liquid dispenser assembly 126 to start and stop in concert with an air conditioning system to automatically supply fragrance to the air while the air conditioner is operational.

Figure 12:
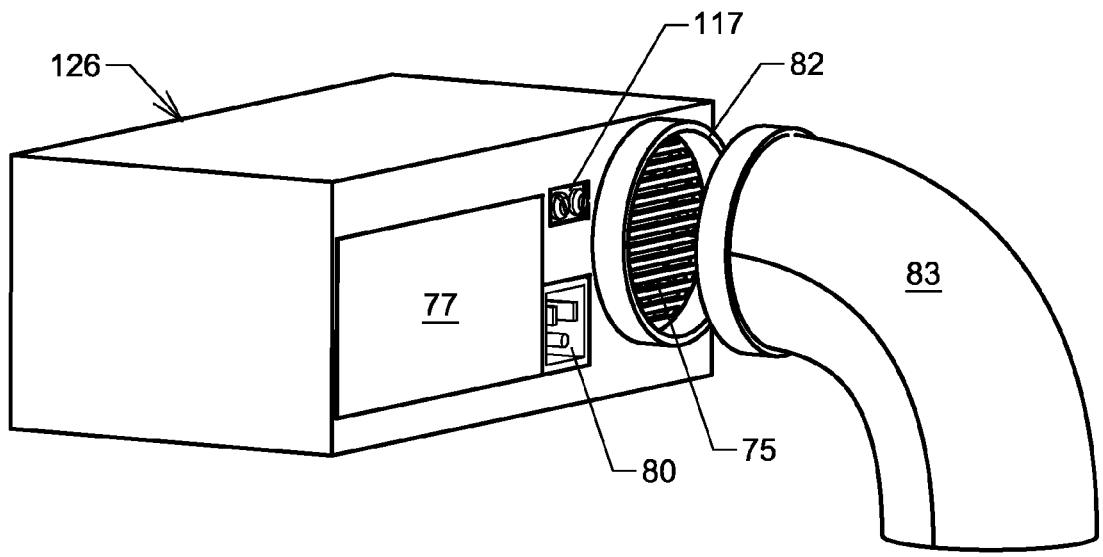
FIG. 12 is a rear perspective view of the invention to demonstrate how a duct can be added to the chassis to direct the output of the device to a desired location, such as through an office ceiling panel.

FIG. 12 is a rear perspective view of the liquid dispenser assembly 126 to demonstrate how a duct 83 can be added to the chassis using a duct coupler 82 to direct the fragrance output of the device to a desired area. For example, the assembly 126 can be mounted in the ceiling area of office building and its output directed through the duct 83 and down through a ceiling panel into office space. The fan inside the assembly 126 can be programmed to reverse direction for this purpose.

Figure 13:
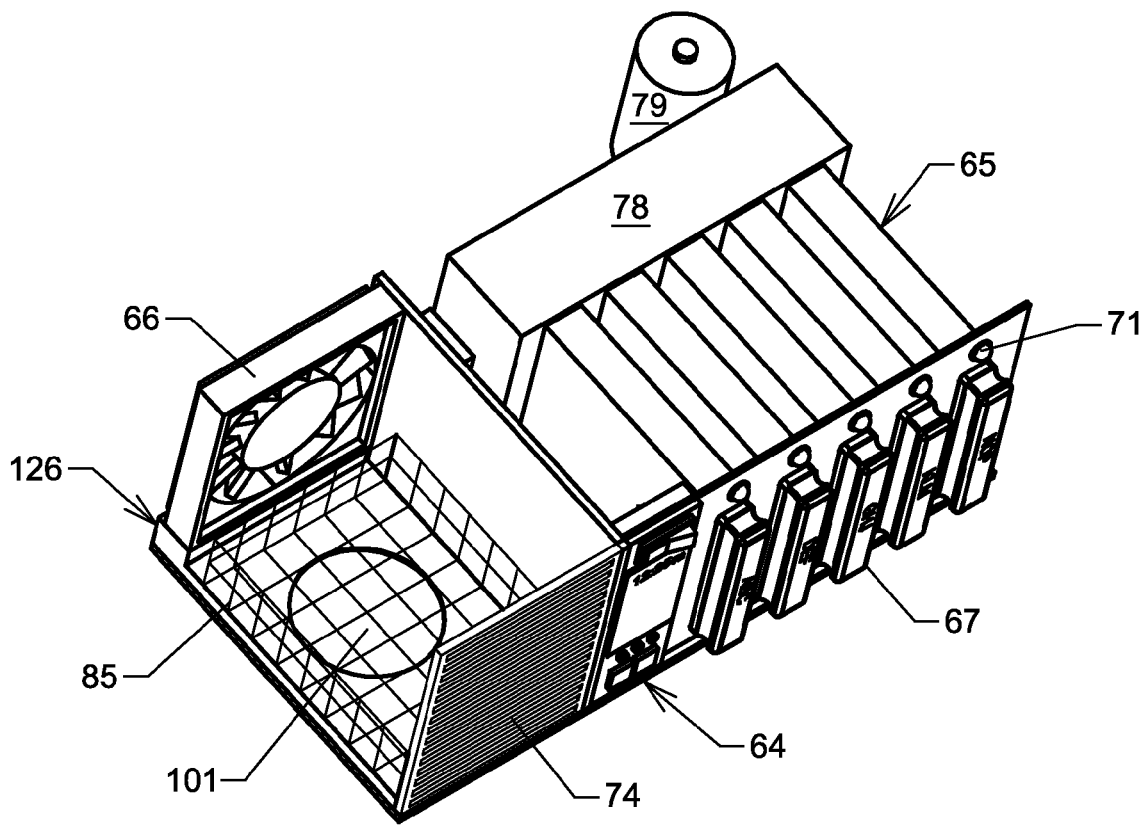
FIG. 13 is a top front perspective view of the invention with its case cover removed to illustrate the components inside.

FIG. 13 is a top front perspective view of the liquid dispenser assembly 126 with its case cover removed to illustrate the components inside. For more clarity, a battery 79 is shown removed from its normal location in the battery tray 78.

Figure 14:
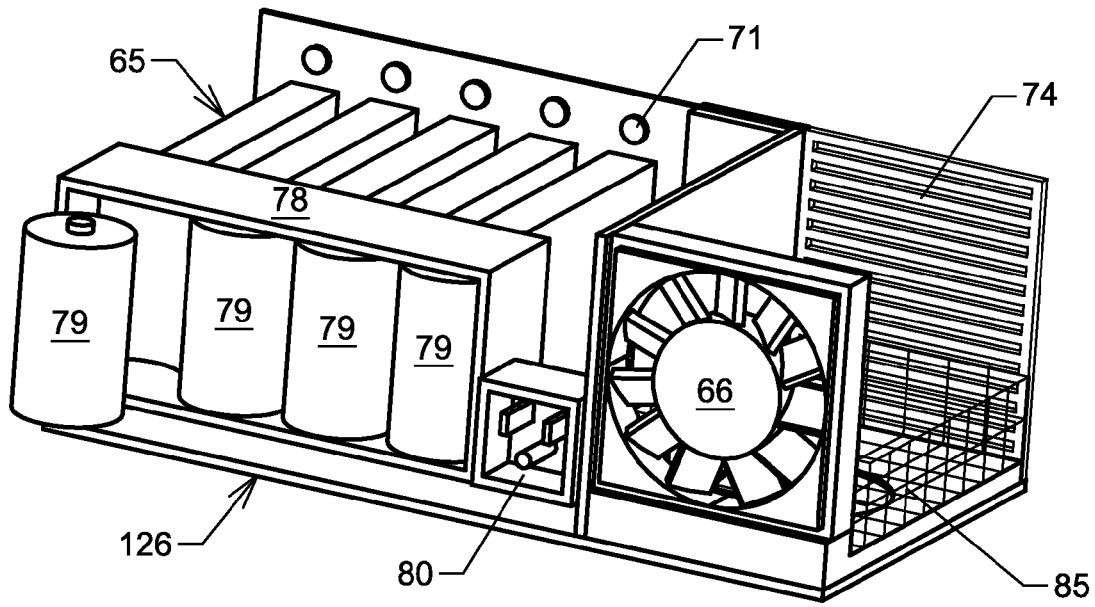
FIG. 14 is a top rear perspective view of the invention with its case cover removed to illustrate the components inside.

FIG. 14 is a rear perspective view of the liquid dispenser assembly 126 with its case cover removed to illustrate the components inside. For more clarity, a battery 79 is shown removed from its normal location in the battery tray 78.

Figure 15:
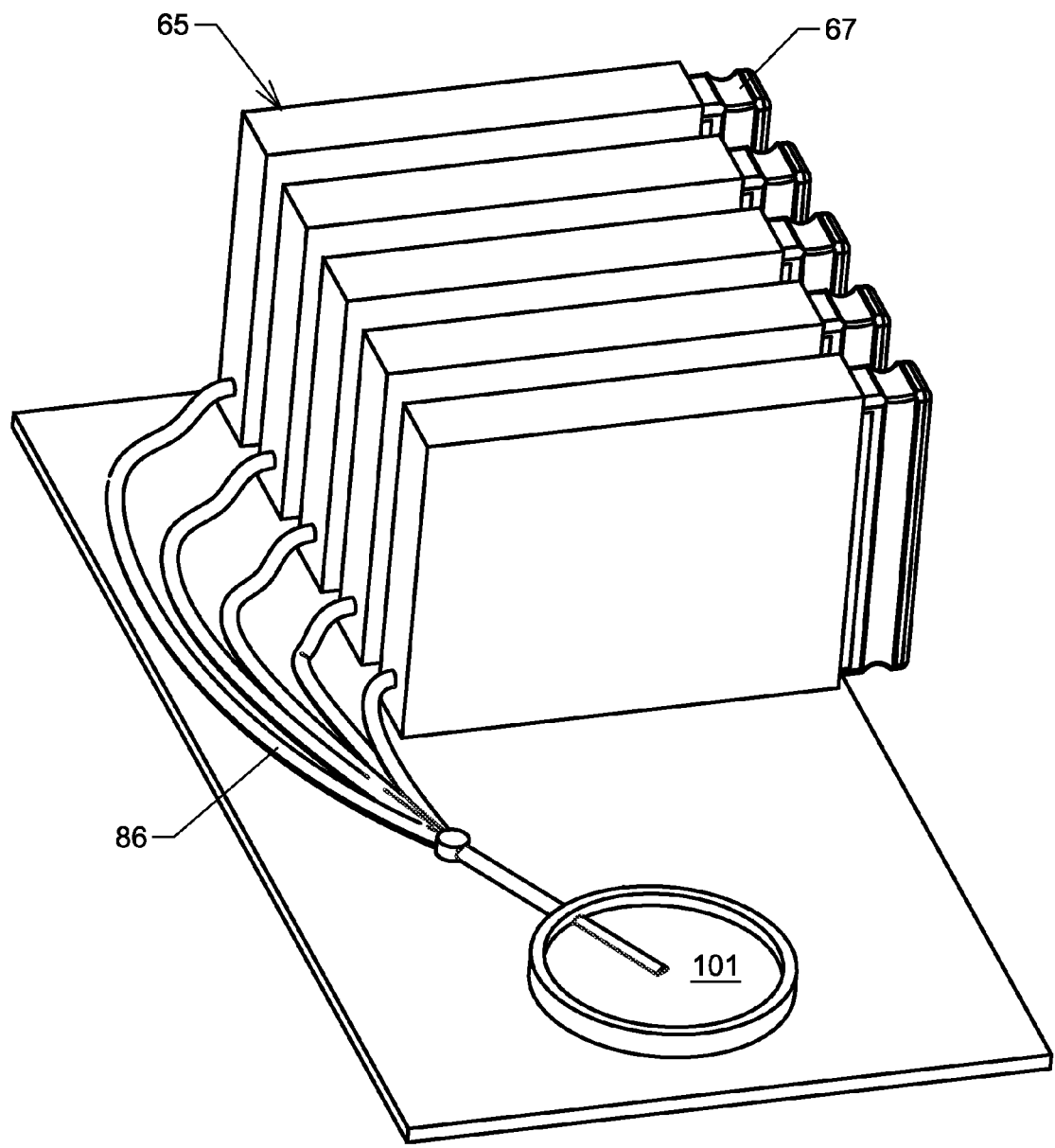
FIG. 15 is a top rear perspective view of an embodiment of the present invention where the output of each liquid pump is directed to a reservoir.

FIG. 15 is a side perspective view of an embodiment of the present invention where the output of each liquid pump assembly 65 is directed to a single reservoir 101 using liquid transfer tubes 86. A very thin layer of metal mesh in this reservoir 101 can absorb and confine the liquid so that it does not flow from the reservoir if the air freshener chassis is tilted. The metal mesh is very porous to allow maximum air movement for evaporation. This reservoir 101 can also contain a heated element to help vaporize any liquid that is deposited there. The heat can be readily transmitted into the metal mesh from the heated element for maximum efficiency.

Figure 16:
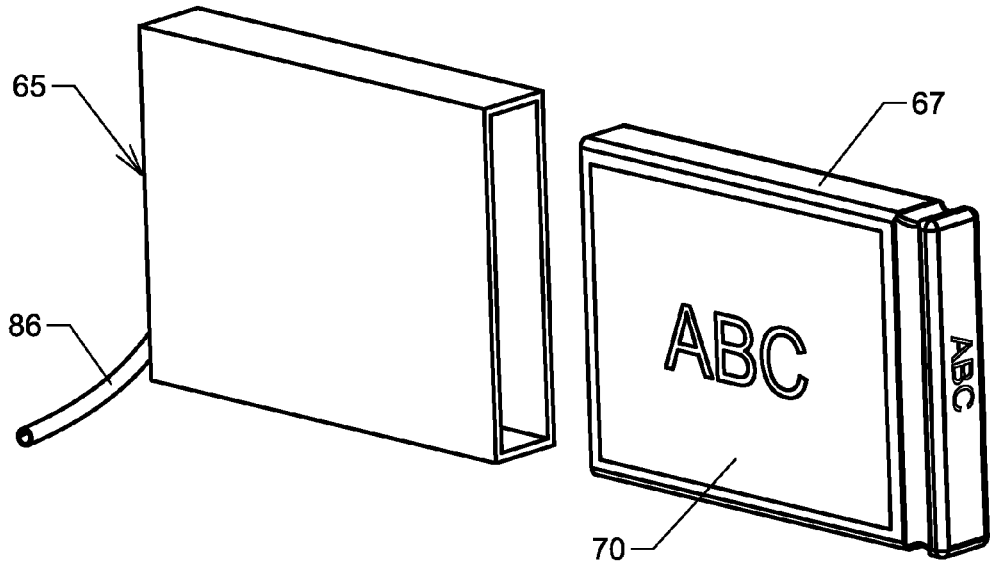
FIG. 16 depicts a cartridge as removed from the liquid pump assembly, where the pump assembly also functions as a mounting sleeve for a cartridge.

FIG. 16 depicts a disposable liquid fragrance cartridge 67 as removed from the liquid pump and cartridge mounting sleeve assembly 65. The cartridge 67 contains a label 70 that specifies its contents.

Figures 17, 18:
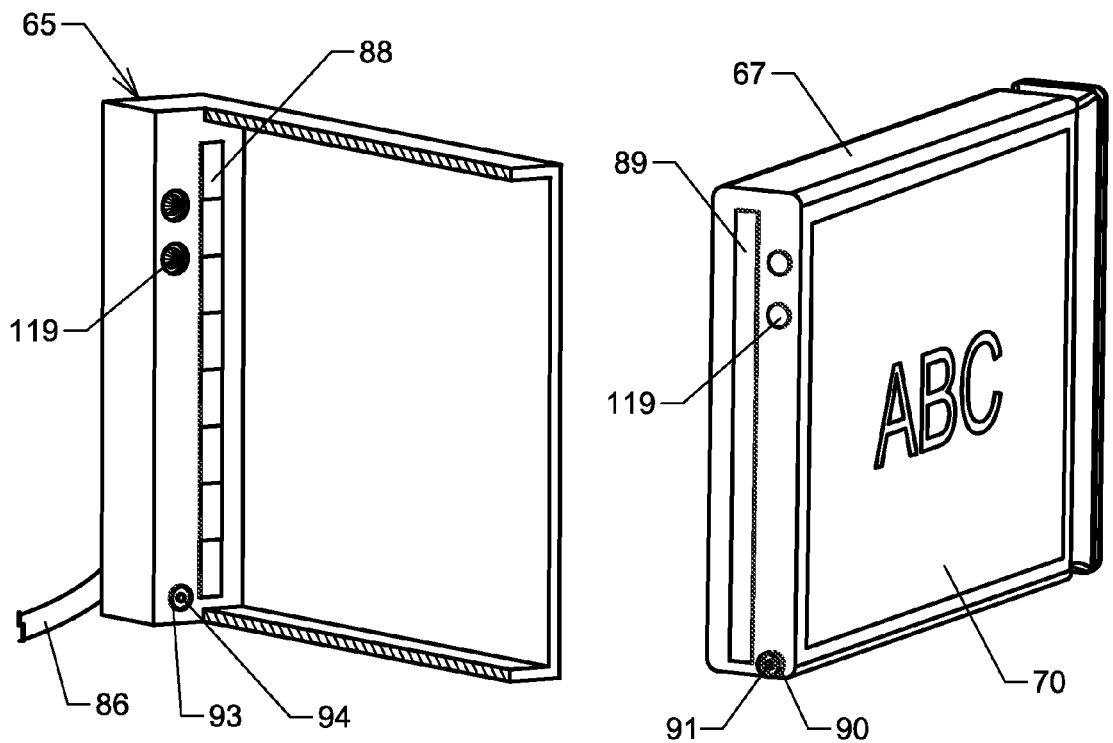
FIG. 17 is a front sectional view of the liquid pump assembly and cartridge mounting sleeve that illustrates the components inside.
FIG. 18 is a rear perspective view a fragrance cartridge.

FIG. 17 is a side sectional view of the liquid pump assembly and cartridge mounting sleeve assembly 65 that illustrates the components inside. Its basic shape contains a cavity that functions as a mounting sleeve to help align and mount a cartridge.

FIG. 18 is a rear perspective view a liquid fragrance cartridge 67. The cartridge 67 contains a label 70 that specifies its contents.

FIG. 17 and FIG. 18 also shows an electronic liquid level sensor 88 on the assembly 65 and a liquid level window pane 89 on the cartridge 67. The pane 89 normally rests within very close proximity to the level sensor 88. The window pane 89 portion of the cartridge 67 is made of a transparent material so that the sensor 88 can detect the level of the fluid inside the cartridge 67. The level sensor 88 communicates with the control module assembly 64 (shown in FIG. 13) so that the fluid level can be known and displayed. The control module assembly 64 can flash a lamp or provide a periodic audible beep to signal a low fluid level condition.

FIG. 17 and FIG. 18 also illustrates the orientation of the mating orifices that communicate the liquid from the cartridge to the pump assembly. The cartridge drain 90 mates with the pump inlet orifice 93. Valve actuator 94 opens the drain valve 91 inside the drain 90 to allow liquid to flow from the cartridge 67 to the pump assembly 65.

FIG. 17 and FIG. 18 also illustrates contacts 119 in assembly 65 that establishes electrical connectivity with mating contacts 119 on the cartridge 67. This feature allows data that is embedded inside the cartridge to be conveyed to the control module assembly 64 (shown in FIG. 13).

Figure 19:
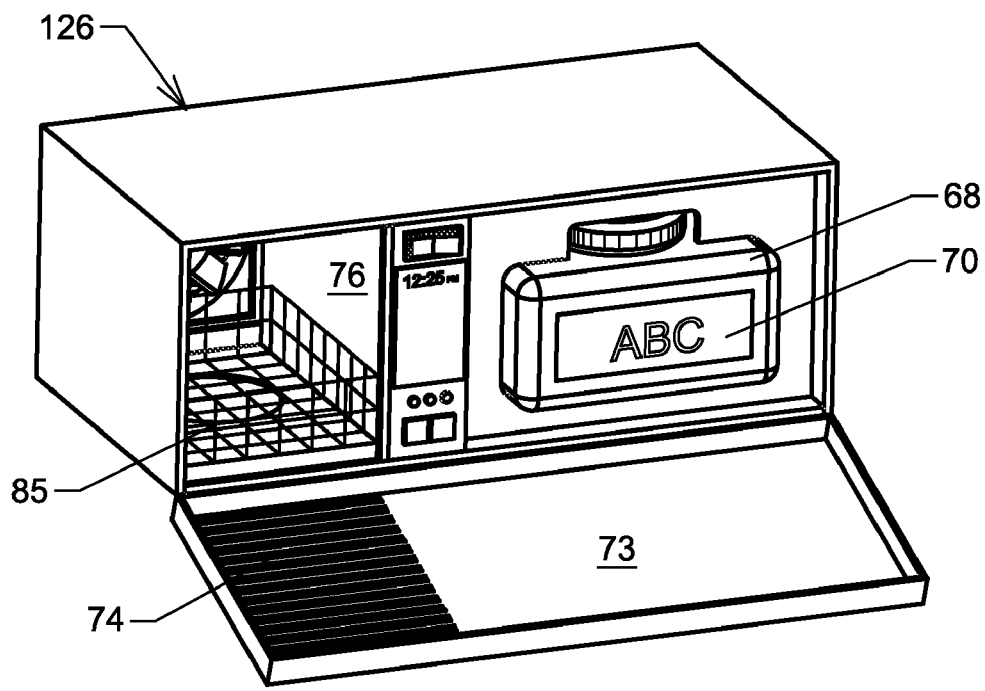
FIG. 19 is a front perspective view of an embodiment of the present invention that illustrates the use of a single refillable fragrance cartridge and a dual-purpose evaporation chamber.

FIG. 19 is a front perspective view of an embodiment of the liquid dispenser assembly 126 that illustrates the use of a single refillable fragrance cartridge 68 and a dual-purpose evaporation chamber 76.

Figure 20:
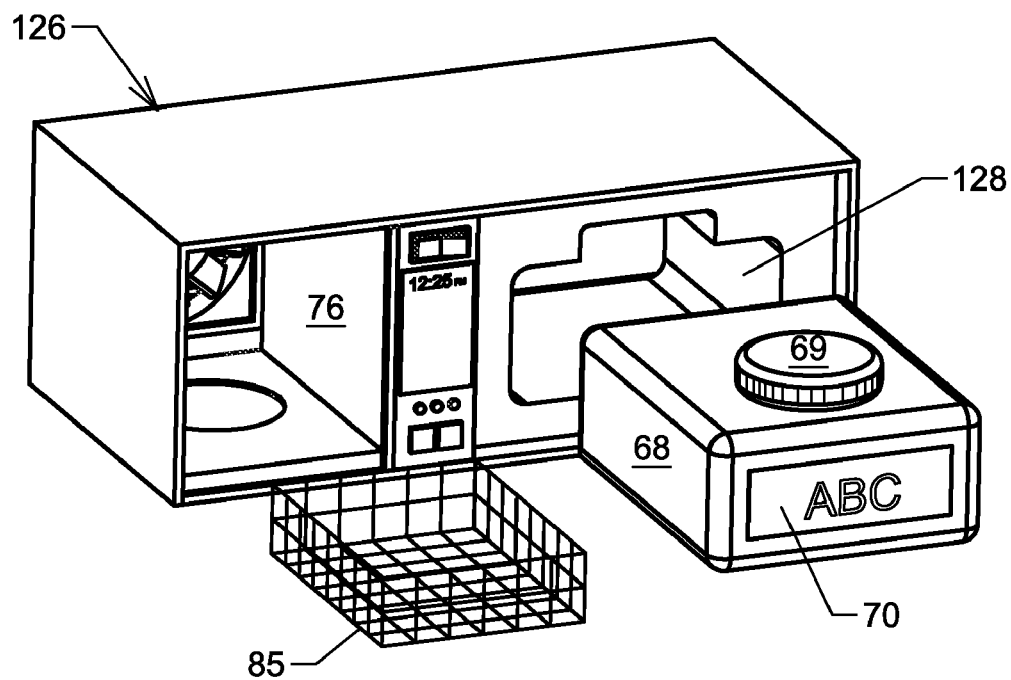
FIG. 20 is the same front perspective view as shown in FIG. 19 but with the cartridge and basket removed to demonstrate their removability.

FIG. 20 is the same front perspective view as shown in FIG. 19 but with the cartridge 68 and basket 85 removed to demonstrate their removability. A cartridge alignment and support guide 128 keeps the cartridge 68 aligned and supported within the assembly 126 so that it can properly mate with the liquid pump assembly that is mounted at the back of the guide 128.

Toilet Mounted Modular Chassis:

FIG. 21-31 illustrates an embodiment the present invention that is formed when a liquid dispenser assembly is mounted in a special modular chassis that is designed to mount onto a standard toilet's water tank.

Figure 21:
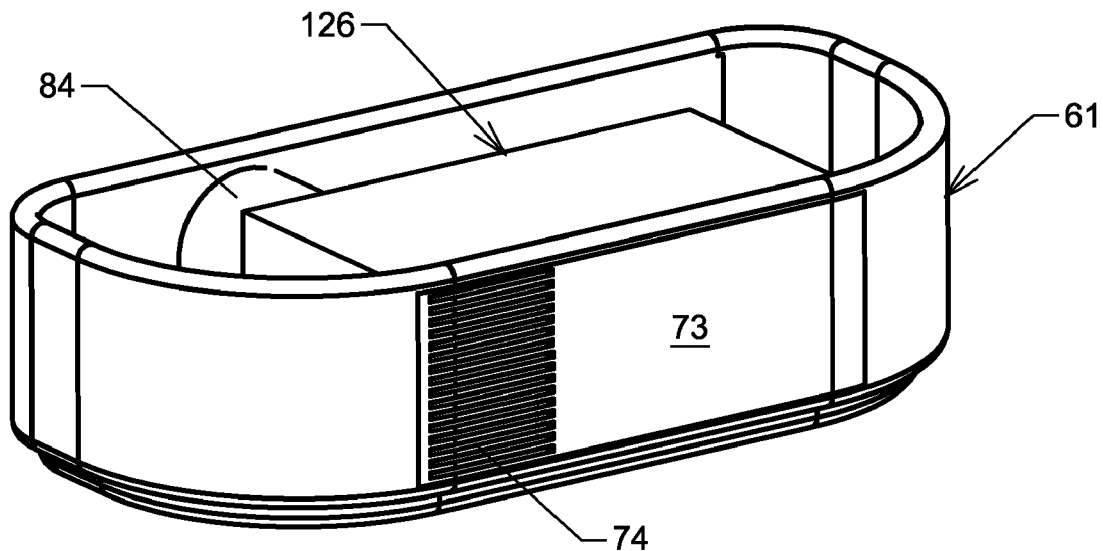
FIG. 21 is a front perspective view of an embodiment of the present invention where it is installed inside a special modular case that is designed to fit onto a toilet water tank.

FIG. 21 is a front perspective view of an embodiment of the present invention where a liquid dispenser assembly 126 is installed inside a special toilet modular chassis assembly 61 that is designed to fit onto a toilet water tank. An air inlet duct 84 provides airflow to the dispenser assembly 126. Fragrance is emitted from the fragrance outlet grill 74.

Figure 22:
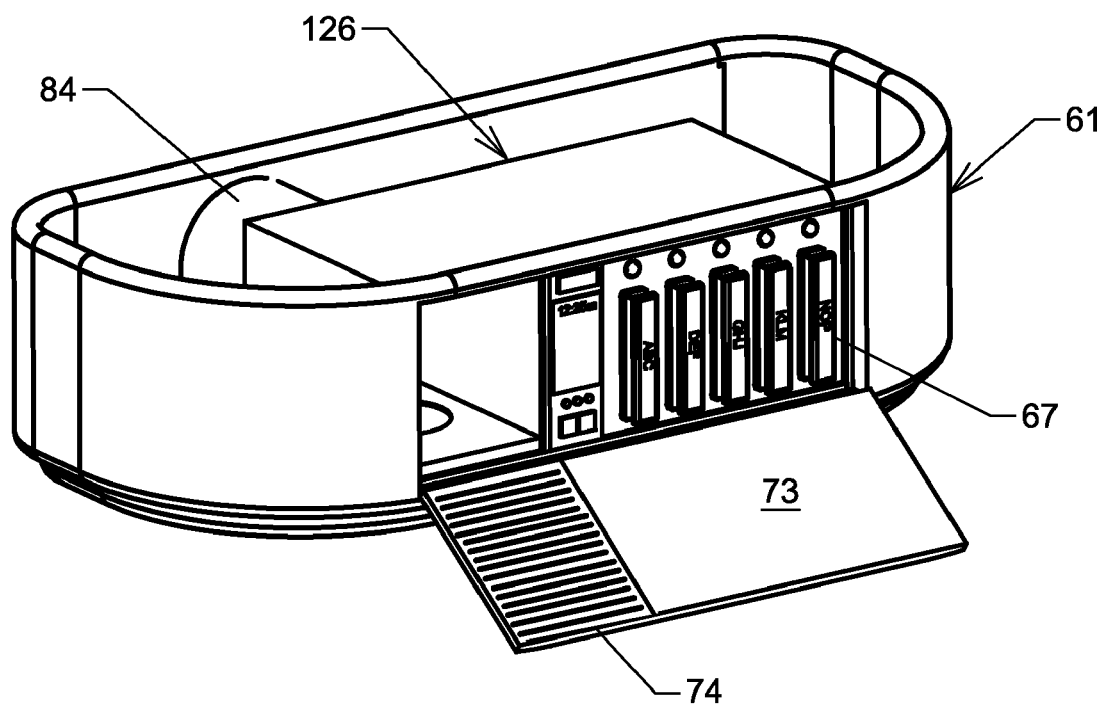
FIG. 22 is the same front perspective view as shown in FIG. 21 but with its front cover hinged open to reveal several installed fragrance cartridges.

FIG. 22 is the same front perspective view as shown in FIG. 21 but with its front cover hinged open to reveal several installed fragrance cartridges 67.

Figure 23:
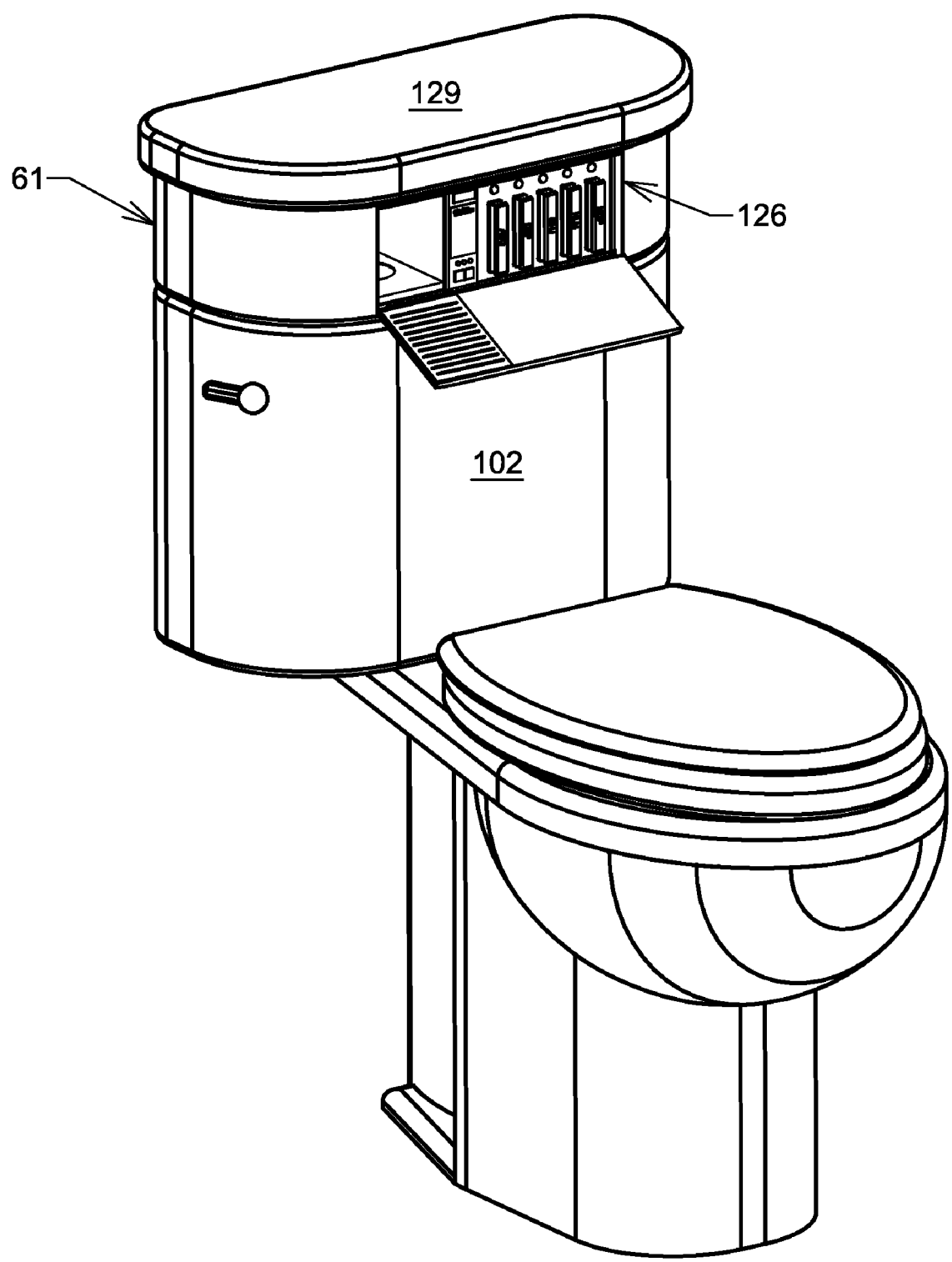
FIG. 23 demonstrates an embodiment of the present invention installed onto a standard toilet's water tank.

FIG. 23 illustrates the basic idea of an embodiment of the present invention where the modular liquid dispenser cabinet assembly 126 is installed inside a special toilet modular chassis 61 and shown mounted onto a standard toilet's water tank 102. The modular chassis 61 is shaped to match the design of the water tank 102 so that it helps blend in with the toilet and décor of the bathroom. The stock water tank lid 129 can be installed onto the modular chassis 61 to help maintain the stock look of the toilet, or a custom tank lid can be used. The modular chassis 61 can also have an integral, non-removable top as well.

Figure 24:
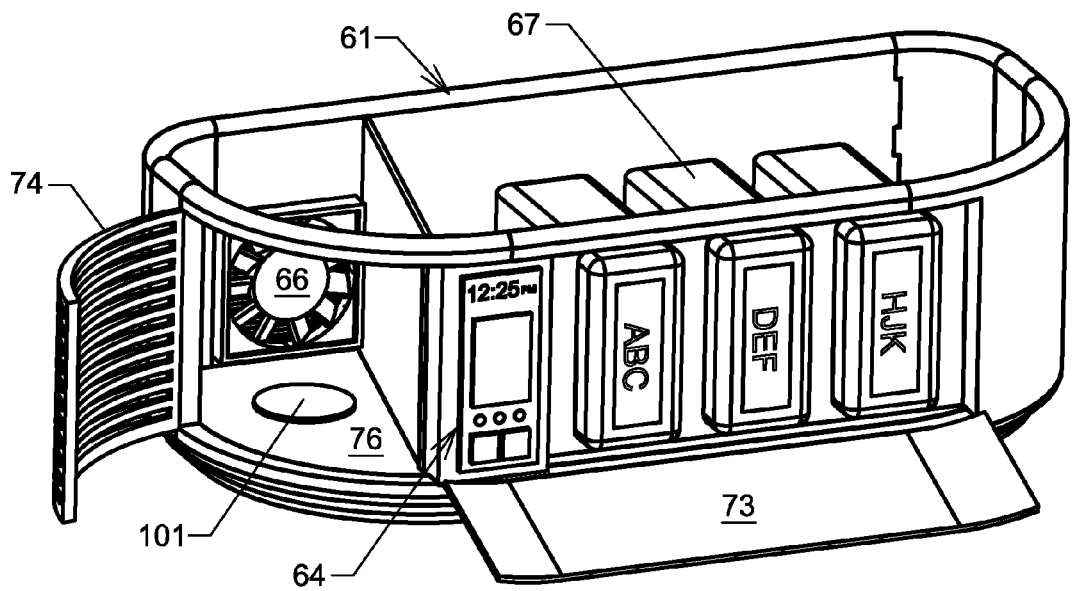
FIG. 24 is a front perspective view of an embodiment of the present invention where a specially designed toilet tank chassis is designed to accommodate three large disposable cartridges.

FIG. 24 is a front perspective view of an embodiment of the present invention where a specially designed toilet tank chassis 61 is designed to accommodate three large disposable cartridges 67. This embodiment also can use a dual-purpose evaporation chamber 76.

Figure 25:
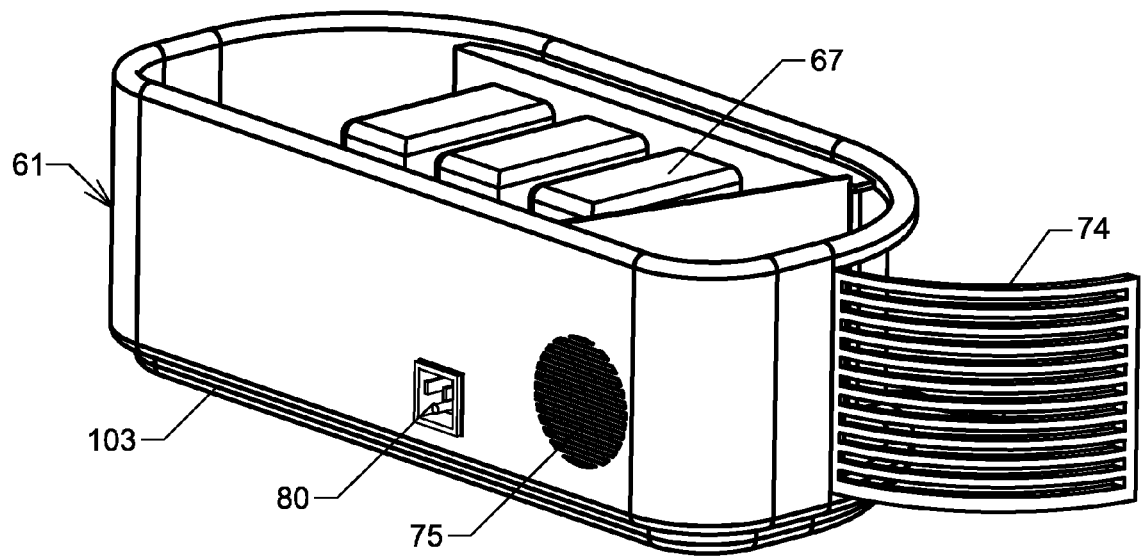
FIG. 25 is a rear perspective view of an embodiment of the present invention where a specially designed toilet tank chassis is designed to accommodate three large disposable cartridges.

FIG. 25 is a rear perspective view of an embodiment of the present invention where a specially designed toilet tank chassis 61 is designed to accommodate three large disposable cartridges 67.

Figure 26:
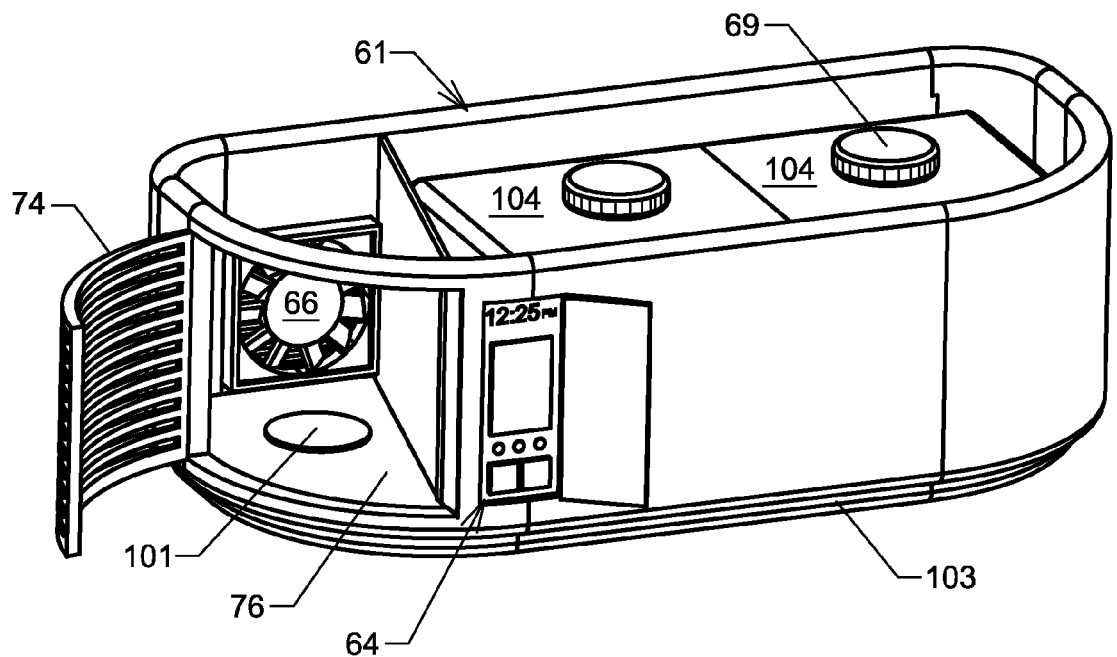
FIG. 26 is a front perspective view of an embodiment of the present invention where a specially designed toilet tank chassis was designed to accommodate a couple of large, fixed mounted liquid holding tanks, instead of removable cartridges.

FIG. 26 is front perspective view of an embodiment of the present invention where a specially designed toilet tank chassis 61 was designed to accommodate a couple of large, fixed mounted liquid holding tanks 104, instead of removable cartridges. These larger tanks 104 can be permanently fixed inside the chassis 61 or can be made to be removable like the cartridge version.

Figure 27:
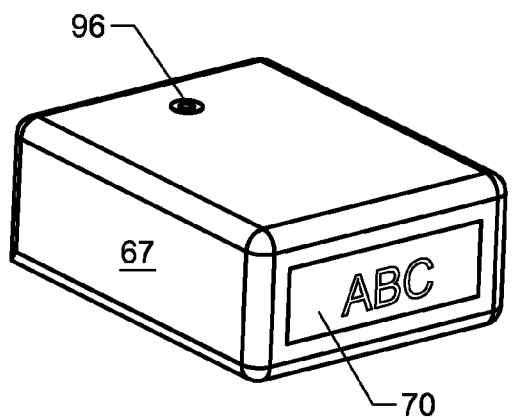
FIG. 27 is a front perspective view of the disposable version of the liquid cartridge with a pressure relief valve located on its top side.

FIG. 27 is a front perspective view of a disposable version of the liquid fragrance cartridge 67. A pressure relief valve 96 allows the flow of air into the cartridge 67 as its solution is consumed. A label 70 is shown affixed to the front of the cartridge 67 to identify its contents.

Another variation of the cartridge shown in FIG. 27 is to use a bladder system, whereby the bladder would reside inside the protective shell of the cartridge. There are some benefits to using a bladder system since liquid can be drawn from it at any angle, without the use of gravity. A pressure relieve valve would not be required. As the bladder's contains is depleted, its size will diminish. The cartridge shell only needs to have perforations to allow air to enter.

Figure 28:
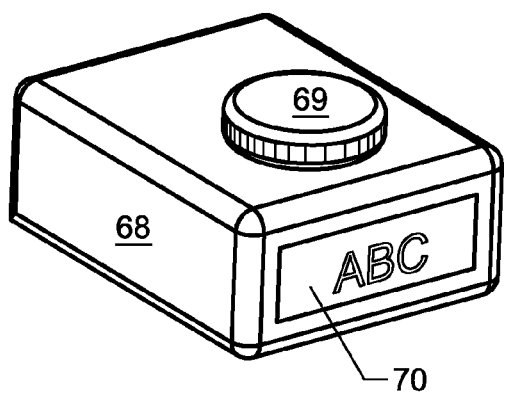
FIG. 28 is a front perspective view of a refillable version of the liquid cartridge that utilizes a ventilated refill cap.

FIG. 28 is a front perspective view of a refillable version of the liquid cartridge 68 shown with its refill cap 69. However, this refillable cartridge 68 can also be disposable. The refill cap 69 can be removed and more solution added. The refill cap 69 is ventilated, which allows the flow of air into the cartridge 68 as its solution is consumed. A label 70 is shown affixed to the front of the cartridge 68 to identify its contents.

FIG. 29 is a side perspective view of a liquid cartridge 68 and liquid pump assembly 125 to show how they would normally be mated together inside a chassis.

FIG. 30 is a rear perspective view of a liquid cartridge 68 and liquid pump assembly 125 to show how they would normally be mated together inside a chassis. A label 70 can be affixed to the cartridge 68 to identify its contents.

FIG. 31 is a perspective view of a liquid cartridge 67 and liquid pump assembly 125 with the liquid pump assembly 125 slightly cocked from the normal alignment with the cartridge 67 to illustrate the orientation of the mating orifices that communicate the liquid from the cartridge 67 to the pump assembly 125. The disposable cartridge 67 (or refillable cartridge 68) can be removed at any time, where a spring loaded drain valve 91 located inside its cartridge drain 90 closes whenever it is pulled away from the pump assembly 125. An "O-ring" type seal 92 around the drain 90 seals against the pump inlet orifice 93. Once the cartridge 67 becomes mated with the pump assembly 125, a valve actuator 94 inside the pump inlet orifice 93 pushes open the drain valve 91 in the cartridge drain 90 to allow liquid to flow from the cartridge 67 into the pump assembly 125.

FIG. 31 also shows an electronic liquid level sensor 88 on the pump assembly 125 and a liquid level window pane 89 on the cartridge 67. The pane 89 normally rests within very close proximity to the level sensor 88. The window pane 89 portion of the cartridge 67 is made of a transparent material so that the sensor 88 can detect the level of the fluid inside the cartridge 67. The level sensor 88 communicates with a control module 64 (shown if FIG. 26) so that the fluid level can be known and displayed. The control module 64 can flash a lamp or provide a periodic audible beep to signal a low fluid level condition.

Yet another method can be used to dispense liquid from the cartridge other than that the method illustrated in FIG. 31. A hollow pin can pierce the cartridge's shell as the cartridge is inserted into the dispenser. Liquid can then be drawn through the pin. The cartridge's shell can be made of a self healing material that can allow for the pin hole to be sealed once the pin is extracted to prevent leaks.

Micro-Sized Liquid Dispensing Air Freshener:

FIG. 32-44 illustrates the embodiments of the present invention where the basic system is mounted into compact, micro-sized chassis that are designed to be extremely portable. These compact chassis are especially designed to work well in automobiles.

Figure 32:
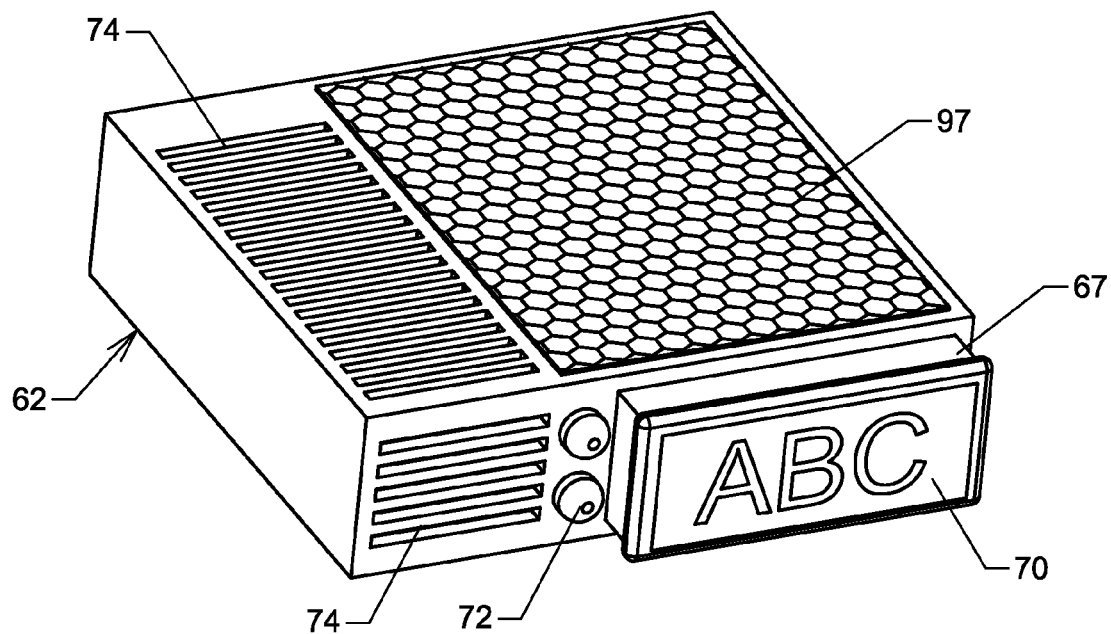
FIG. 32 is a top front perspective view of an embodiment of the present invention that uses a portable, micro-sized chassis. A solar cell is used on its top surface as a power source.

FIG. 32 is a front perspective view of an embodiment of the present invention that uses a portable, micro-sized chassis. This micro liquid dispenser assembly 62 can accept at least one cartridge 67. An optional solar panel 97 is shown on the dispenser assembly 62 as a power source.

Figure 33:
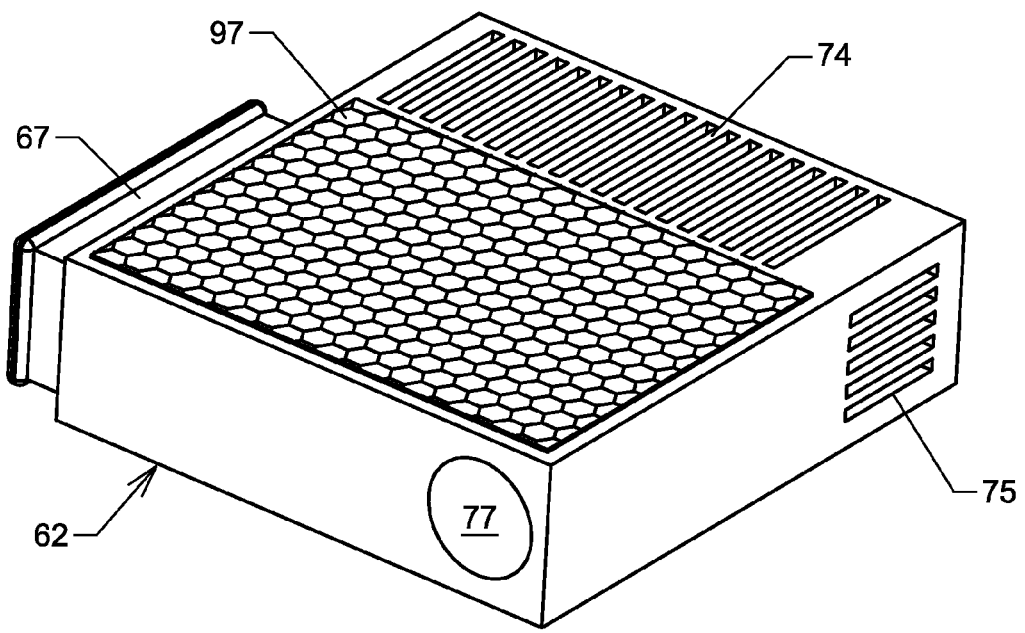
FIG. 33 is a top rear perspective view of an embodiment of the present invention that uses a portable, micro-sized chassis. A solar cell is used on its top surface as a power source.

FIG. 33 is a rear perspective view of an embodiment of the present invention that uses a portable, micro-sized chassis. This micro liquid dispenser assembly 62 can accept at least one cartridge 67. An optional solar panel 97 is shown on the dispenser assembly 62 as a power source.

Figure 34:
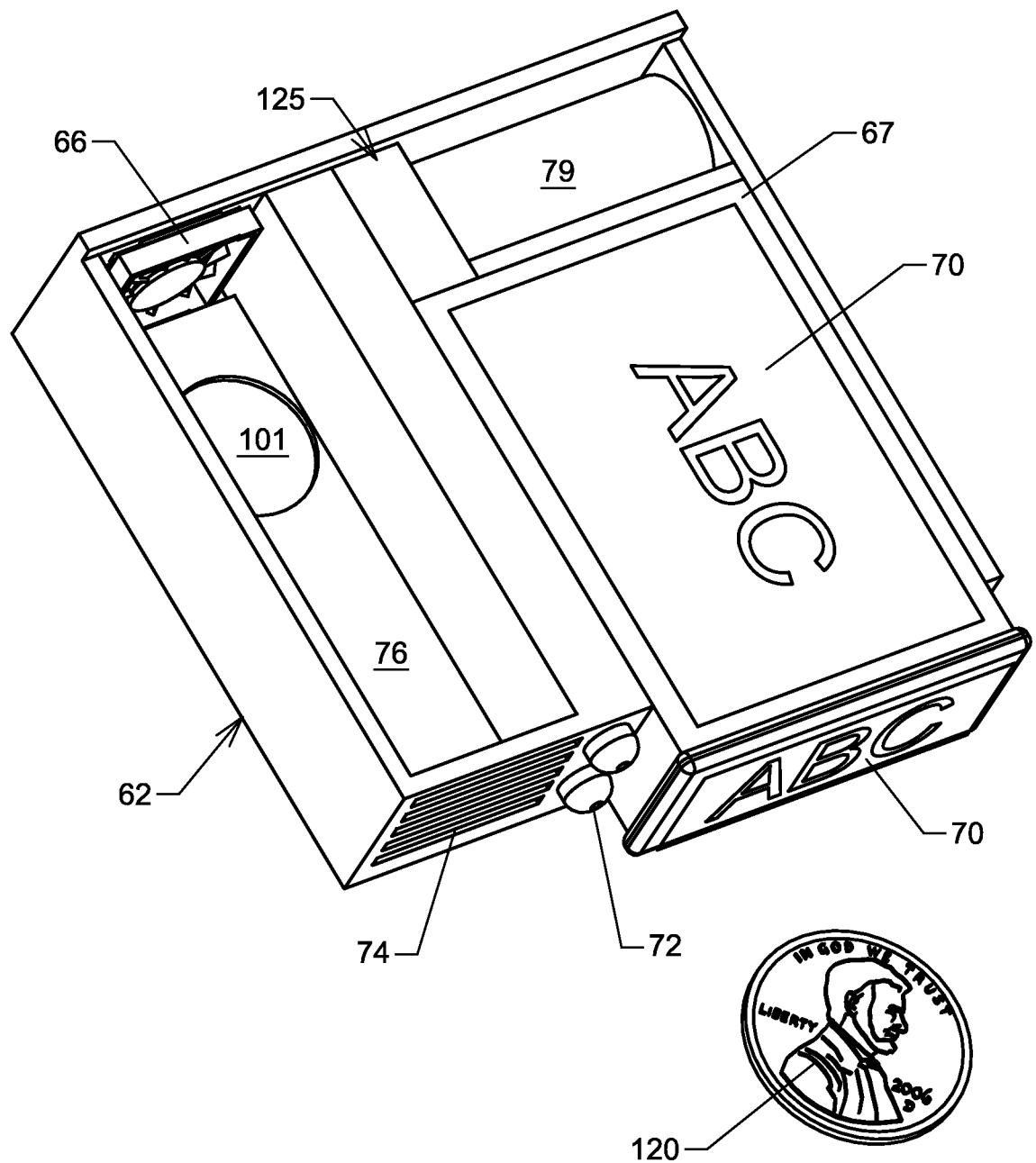
FIG. 34 is a front perspective view of the present invention that uses a portable, micro-sized chassis with its top cover removed to illustrate the components inside.

FIG. 34 is a front perspective view of the portable, micro liquid dispenser assembly 62 with its top cover removed to illustrate the components inside. A battery 79 provides power for the dispenser assembly 62. A rechargeable battery can also be used, where a solar panel 97 (shown in FIG. 33) can keep it charged. Liquid pump 125 dispenses liquid from the cartridge 67 into the reservoir 101 that is located inside the evaporation chamber 76. A fan 66 will push air over the reservoir 101 to evaporate the liquid and propel fragrance through the outlet grill 74. Switch 72 allows for control and selection of programmed functions. A penny 120 is shown next to the assembly 62 as a scale reference to emphasize the tiny size of the device.

FIG. 35 is a top view of the micro liquid dispenser assembly 62 that uses a portable, a micro-sized chassis. Solar panel 97 is used to supply power. Fragrance can also be propelled through the top outlet grill 74.

FIG. 36 is a side view of the micro liquid dispenser assembly 62 that uses a portable, a micro-sized chassis.

FIG. 37 is a front view of the micro liquid dispenser assembly 62 that uses a portable, a micro-sized chassis.

FIG. 38 is a rear view of the micro liquid dispenser assembly 62 that uses a portable, a micro-sized chassis.

Figure 39:
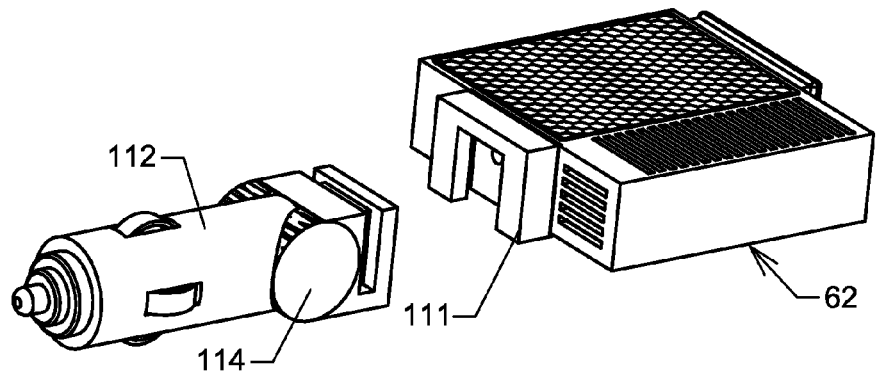
FIG. 39 illustrates how a removable mounting shoe on the portable, micro-sized chassis can be used to attach it to a cigarette lighter power adapter.

FIG. 39 illustrates how a removable mounting shoe 111 on a micro liquid dispenser assembly 62 can be used to attach it to a cigarette lighter power adapter 112.

Figure 40:
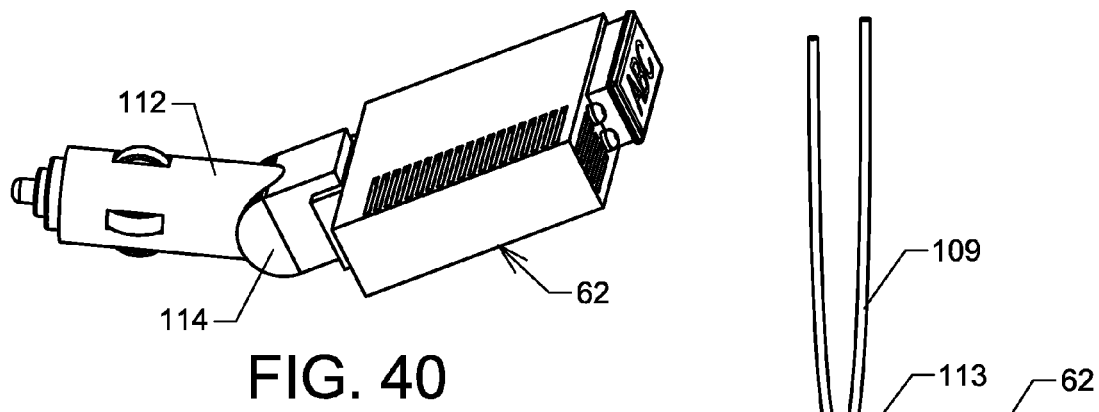
FIG. 40 illustrates a hinged joint in the cigarette lighter adapter can allow the portable, micro-sized chassis to be pivoted to any desired angle.

FIG. 40 illustrates a hinged joint 114 in the cigarette lighter adapter 112 can allow a micro liquid dispenser assembly 62 to be pivoted to any desired angle.

Figure 41:
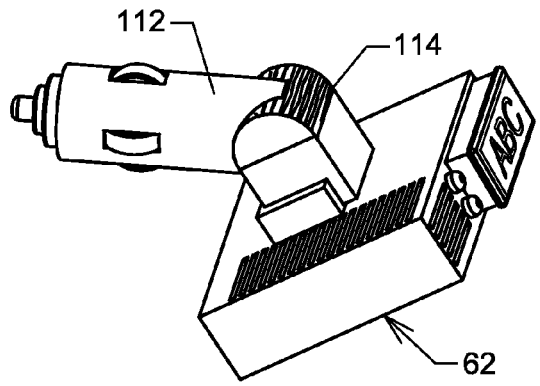
FIG. 41 illustrates another mounting position for the removable mounting shoe on the portable, micro-sized chassis to allow a cigarette lighter power adapter to pivot it to any desired angle.

FIG. 41 illustrates another mounting position for the removable mounting shoe 111 on a micro liquid dispenser assembly 62 to allow a cigarette lighter power adapter 112 to pivot it to any desired angle.

Figure 42:
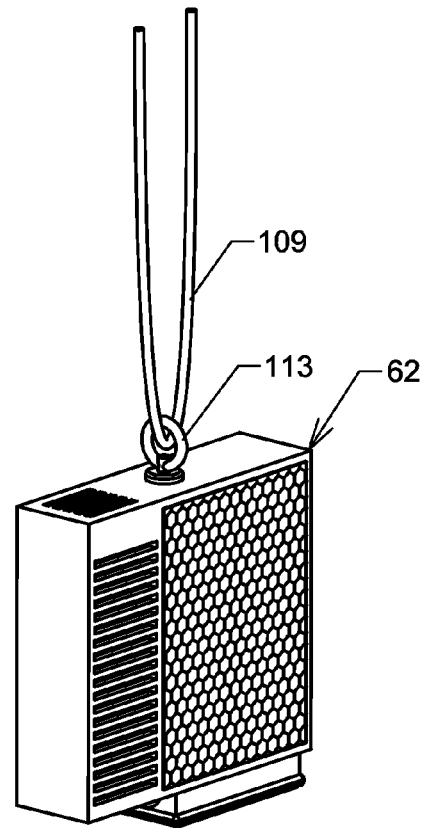
FIG. 42 illustrates how the micro-sized chassis can be hung from an eyelet.

FIG. 42 illustrates how micro liquid dispenser assembly 62 can be hung from an eyelet 113 by using a cord 109.

Figure 43:
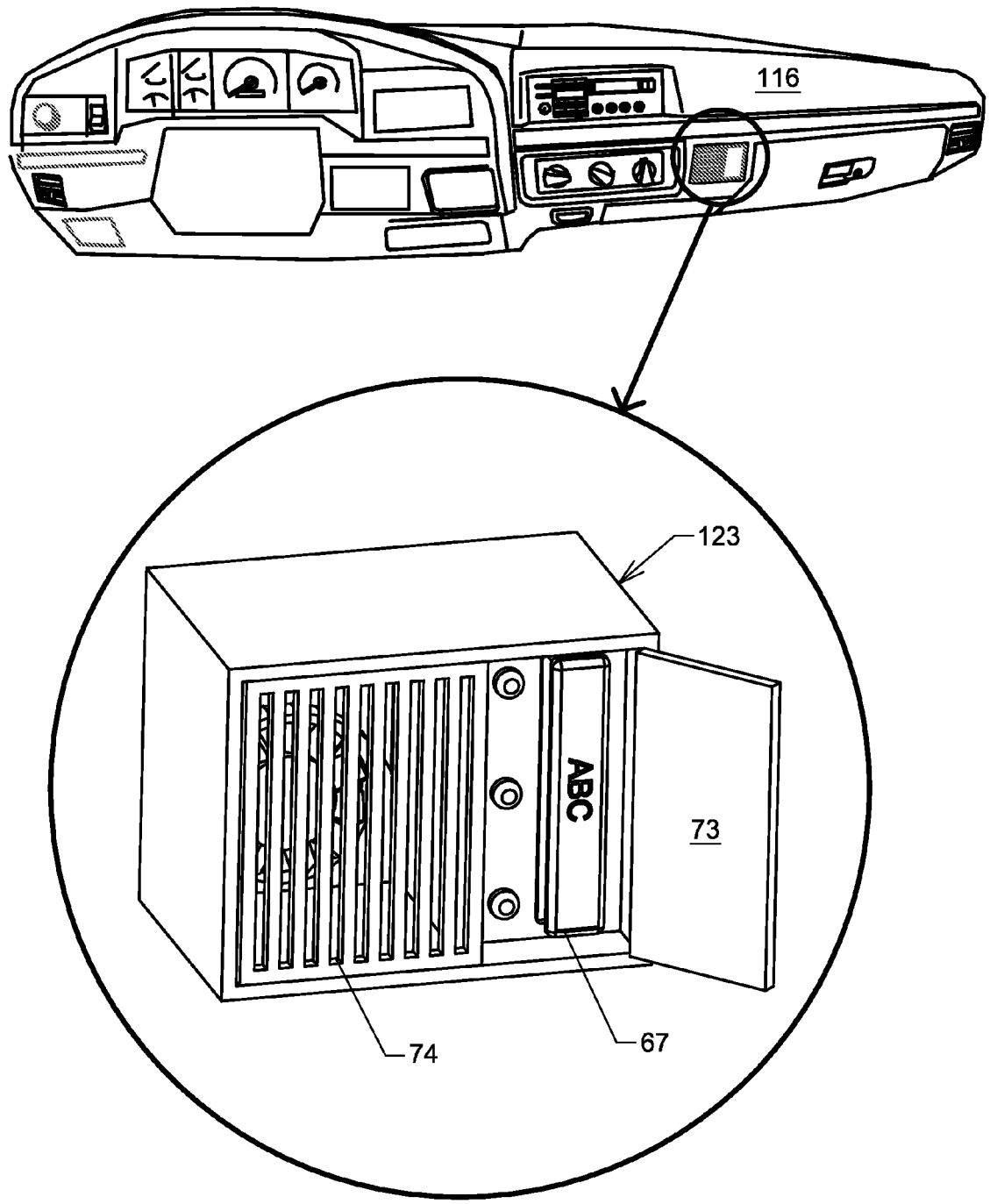
FIG. 43 is a diagram of a compact version of the present invention as installed into an automobile's dash panel.

FIG. 43 is a diagram of car dash mounted chassis assembly 123 can be designed to fit into an automobile's dash panel 116. This embodiment of the present invention is shown with a front outlet grill 74. It can also be made to discharge fragrance directly into the car's air conditioning ductwork so that the fragrance can be more evenly distributed though the vehicle.

Figure 44:
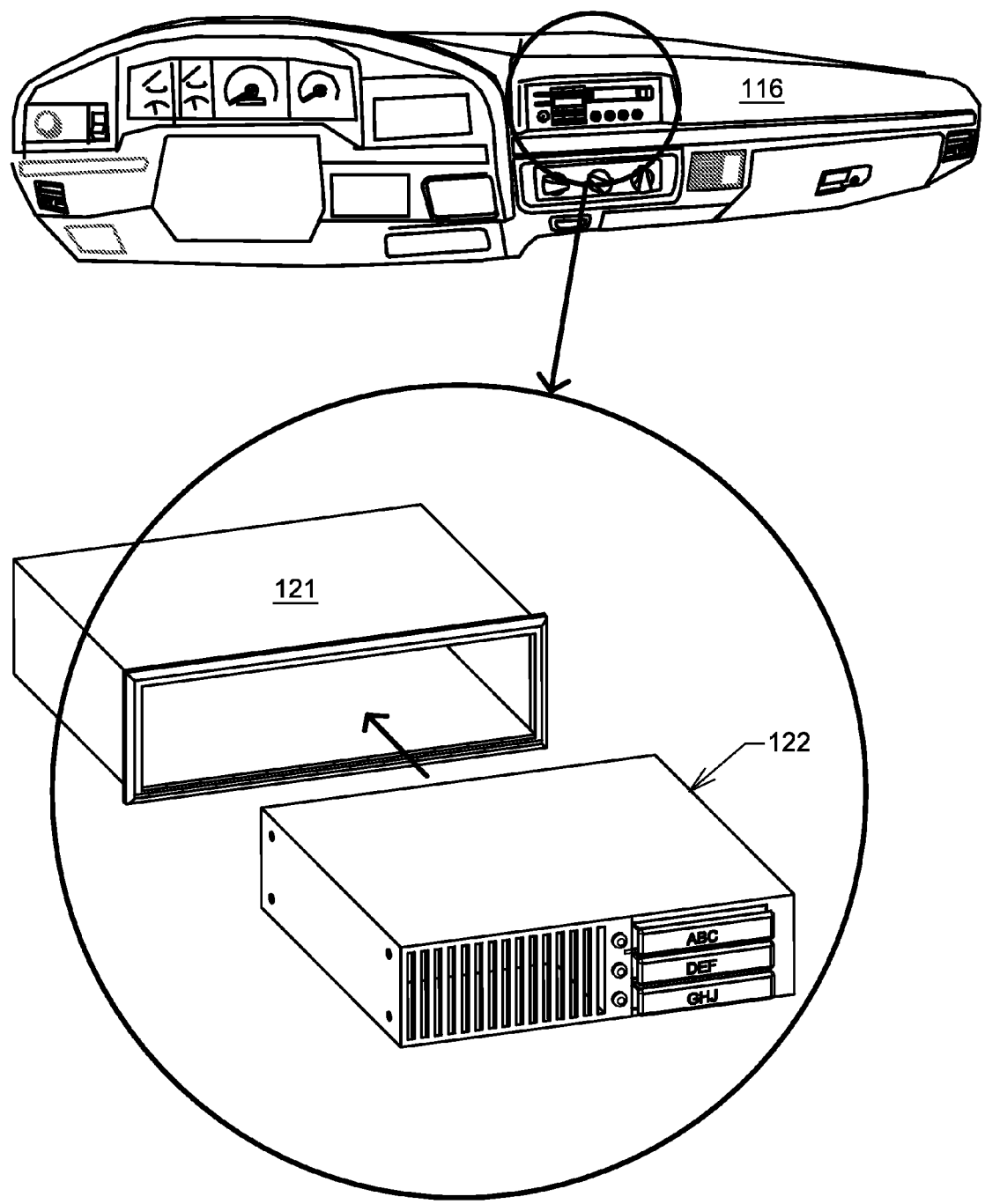
FIG. 44 is a diagram of the present invention as installed into an automobile's stereo area, where the air freshener chassis is specially shaped to fit into a standard stereo mounting sleeve.

FIG. 44 is a diagram of an embodiment of the present invention where the liquid dispenser system's chassis is specially shaped into a car air freshener stereo replacement chassis 122. This specially shaped chassis will fit into a standard stereo mounting sleeve 121 so that it can be quickly and easily installed into the stereo area of an automobile's dash panel 116. This unique air freshener embodiment can be used anywhere a standard stereo system is used.

Micro-Sized Plug-In Liquid Dispensing Air Freshener:

FIG. 45-53 illustrate an embodiment of the present invention that uses a compact, micro-sized wall receptacle plug-in chassis. This compact chassis allows the air freshener to be plugged into any standard power receptacle.

Figure 45:
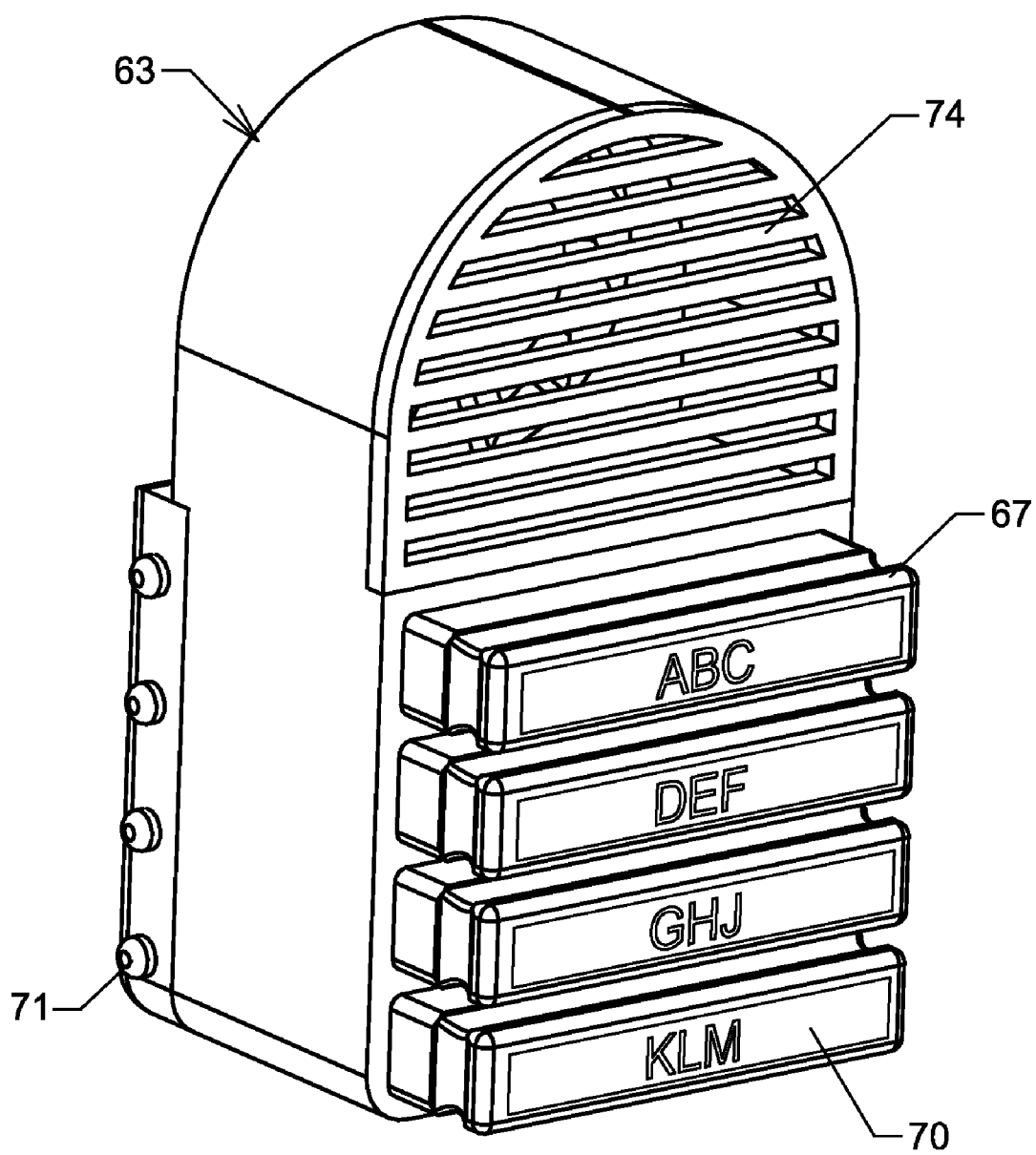
FIG. 45 a front perspective view of an embodiment of the present invention where a specially designed compact, micro-chassis is shaped and configured to work as a wall receptacle plug-in, with its front cartridge access cover removed to show several installed cartridges.

FIG. 45 a front perspective view of an embodiment of the present invention where a specially designed compact, micro-chassis is shaped and configured to work as a wall receptacle plug-in. This wall cartridge-based liquid dispenser assembly 63 is shown with its front cartridge access cover removed to show several installed cartridges 67. Fragrance is emitted from the fragrance outlet grill 74. Lighted switches 71 allows a user to select (or deselect) the assembly 63 for operation and illuminates to indicate its operational status.

Figure 46:
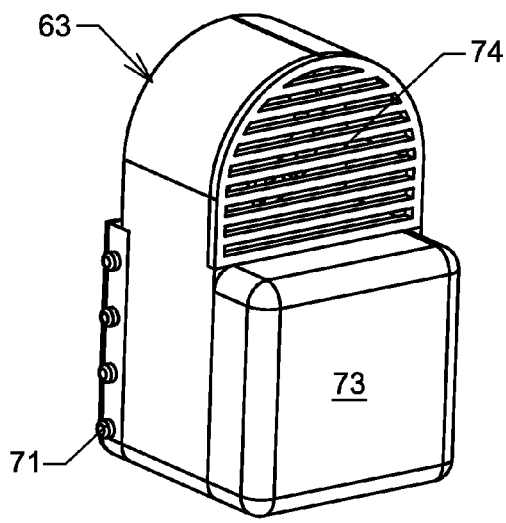
FIG. 46 a front perspective view of an embodiment of the present invention where a specially designed compact, micro-chassis is shaped to work as a wall receptacle plug-in, with is front cartridge access cover installed.

FIG. 46 a front perspective view of an embodiment of the present invention where a specially designed compact, micro-chassis is shaped and configured to work as a wall receptacle plug-in. This wall cartridge-based liquid dispenser assembly 63 is shown with its front assembly cover 73 installed. Fragrance is emitted from the fragrance outlet grill 74. Lighted switches 71 allows a user to select (or deselect) the assembly 63 for operation and illuminates to indicate its operational status.

Figure 47:
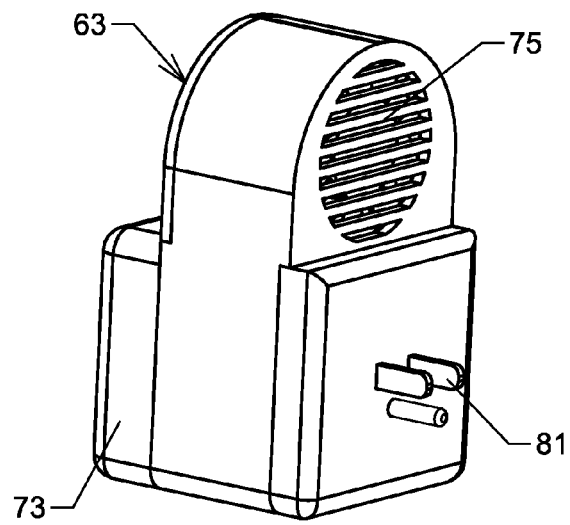

FIG. 47 is a rear perspective view of an embodiment of the present invention where a specially designed compact, micro-chassis is shaped and configured to work as a wall receptacle plug-in. This wall cartridge-based liquid dispenser assembly 63 is shown with electrical plug 81 that provides power to the unit and supports its chassis in a standard wall receptacle. Air is drawn into the assembly 63 though the air inlet 75.

Figure 48:
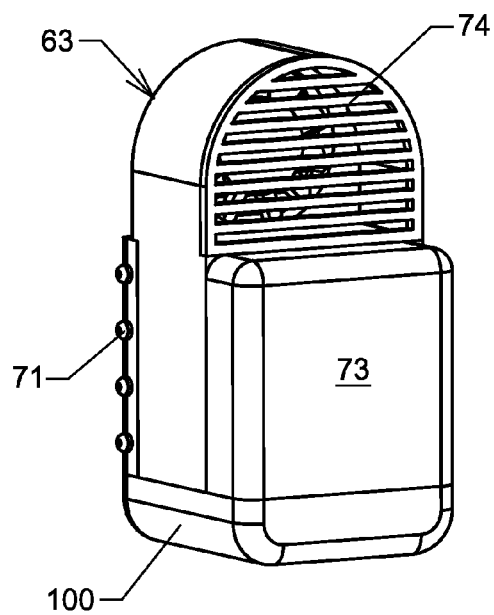
FIG. 48 a front perspective view of an embodiment of the present invention where a specially designed compact, micro-chassis is shaped to work as a wall receptacle plug-in that includes a night light that is mounted on its bottom edge.

FIG. 48 a front perspective view of an embodiment of the present invention where a specially designed compact, micro-chassis is shaped and configured to work as a wall receptacle plug-in that includes a night light 100 that is mounted on its bottom edge. This wall cartridge-based liquid dispenser assembly 63 is shown with its front assembly cover 73 installed. Fragrance is emitted from the fragrance outlet grill 74. Lighted switches 71 allows a user to select (or deselect) the assembly 63 for operation and illuminates to indicate its operational status.

Figure 49:
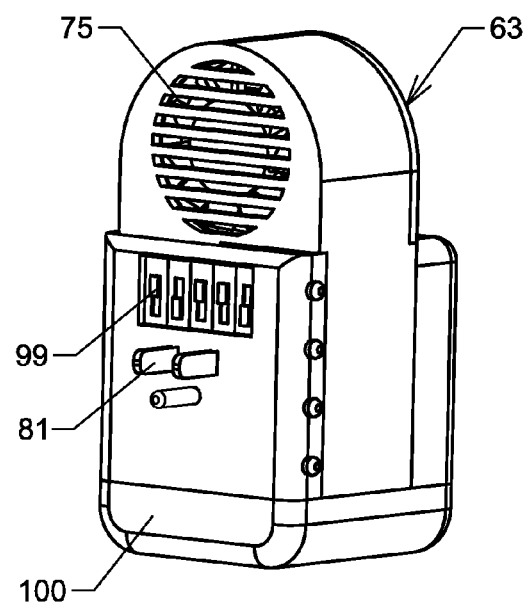
FIG. 49 a rear perspective view of an embodiment of the present invention where a specially designed compact, micro-chassis is shaped to work as a wall receptacle plug-in that includes a night light that is mounted on its bottom edge.

FIG. 49 a rear perspective view of an embodiment of the present invention where a specially designed compact, micro-chassis is shaped and configured to work as a wall receptacle plug-in that includes a night light 100 that is mounted on its bottom edge. This wall cartridge-based liquid dispenser assembly 63 is shown with electrical plug 81 that provides power to the unit and supports its chassis in a standard wall receptacle. Air is drawn into the assembly 63 though the air inlet 75. A switch programming panel 99 allows a user the capability to program the device. A more sophisticated control panel with an alphanumerical display can also be used to simplify programming effort.

Figure 50:
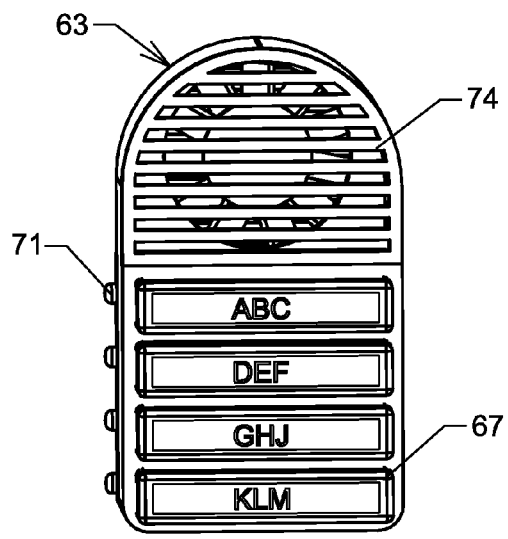

FIG. 50 is a front view of an embodiment of the present invention where a specially designed compact, micro-chassis is shaped and configured to work as a wall receptacle plug-in. This wall cartridge-based liquid dispenser assembly 63. Fragrance is emitted from the fragrance outlet grill 74. Lighted switches 71 allows a user to select (or deselect) the assembly 63 for operation and illuminates to indicate its operational status.

Figure 51:
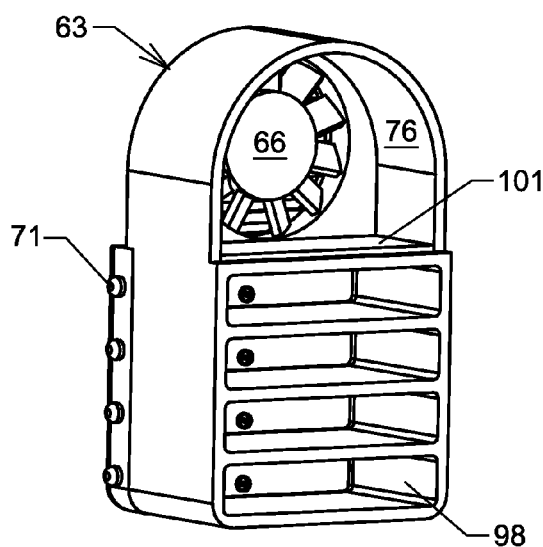
FIG. 51 a front perspective view of an embodiment of the present invention where a specially designed compact, micro-chassis is shaped to work as a wall receptacle plug-in with the cartridges and fragrance outlet grill removed.

FIG. 51 is the same front perspective view as shown in FIG. 45, but now the wall cartridge-based liquid dispenser assembly 63 has its cartridges 67 and fragrance outlet grill 74 removed to illustrate the components inside.

Figure 52:
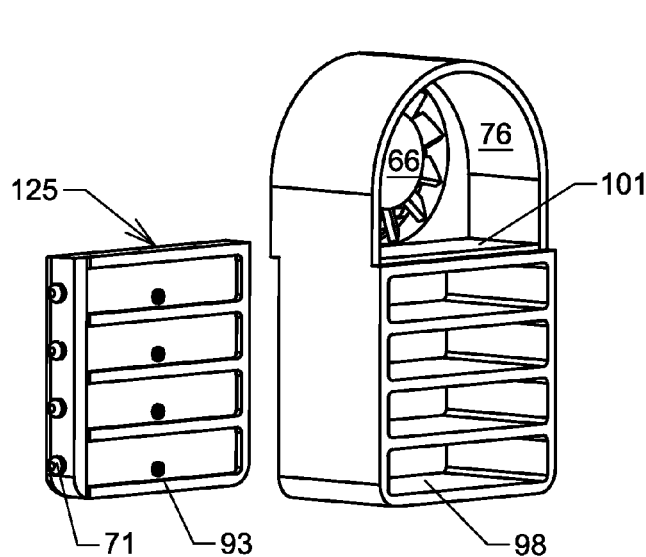
FIG. 52 is the same front perspective view as shown in FIG. 51 but now with the liquid pump assembly removed.

FIG. 52 is the same front perspective view as shown in FIG. 51 but now the wall cartridge-based liquid dispenser assembly 63 has its liquid pump assembly 125 removed to illustrate the components inside.

Figure 53:
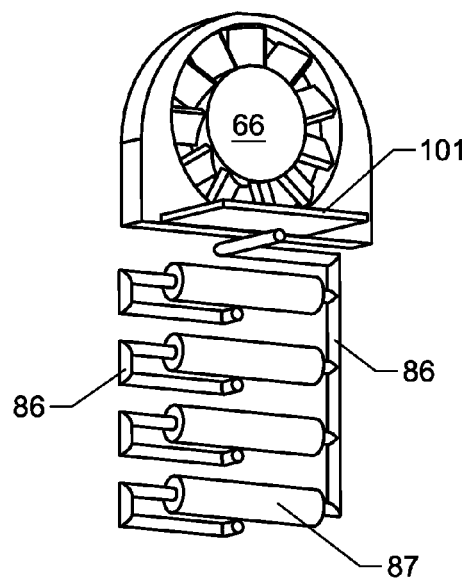
FIG. 53 is a functional diagram of the liquid pumping system of the wall receptacle plug-in embodiment of the present invention and how the liquid is routed to a reservoir in front of a fan.

FIG. 53 is a functional diagram of the liquid pumping system of the wall receptacle plug-in embodiment of the present invention and how the liquid is routed. Liquid pumps 87 operate to pump liquid from cartridges 67 into liquid transfer tubes 86 through the pumps 87 and finally on into a liquid reservoir 101 that is positioned in front of a fan 66.

Figure 54:
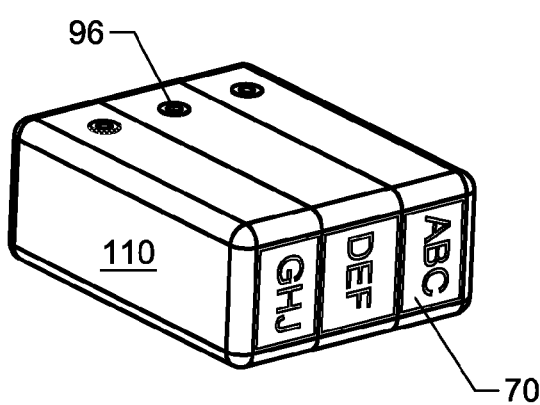
FIG. 54 is a front perspective view of a multiple compartment cartridge.

Multiple Chamber Cartridges:

FIG. 54 is a front perspective view of a multiple compartment cartridge 110. This cartridge 110 has three separate compartments, each of which can store a different fragrance. A single cartridge with multiple fragrances can offer a user more convenience without having to handle multiple cartridges.

Figure 55:
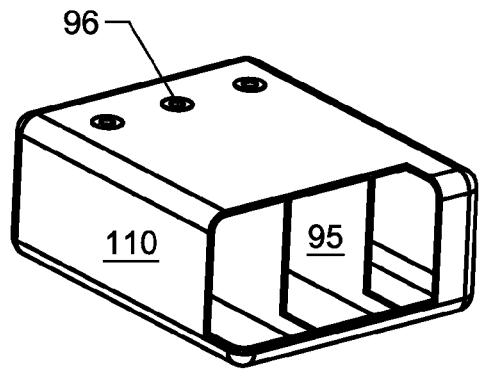
FIG. 55 is a sectional view of a multiple compartment cartridge to illustrate its several compartments that are used to store different fragrances.

FIG. 55 is a sectional view of a multiple compartment cartridge 110 to illustrate its several compartments 95 that are used to store different fragrances.

Figure 56:
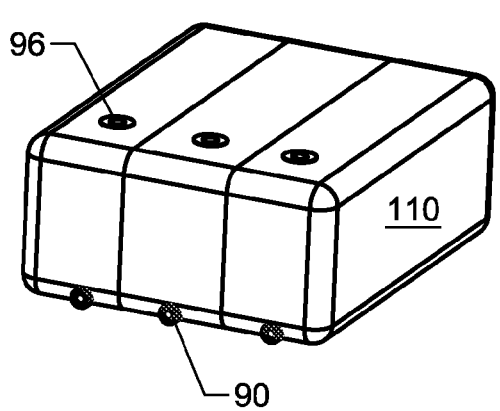
FIG. 56 is a rear perspective view of a multiple compartment cartridge to illustrate its multiple drains, where each compartment is provided with its own separate drain.

FIG. 56 is a rear perspective view of a multiple compartment cartridge 110 to illustrate its multiple drains 90, where each of the compartments is provided with its own drain 90.

Figure 57:
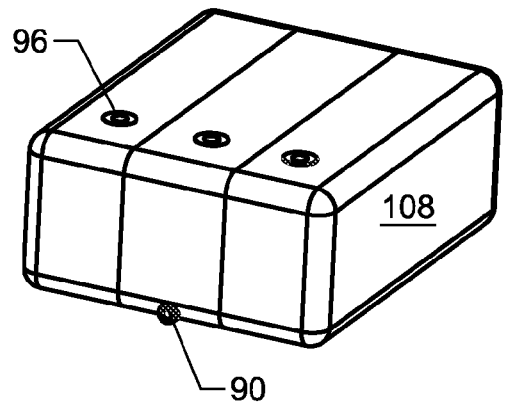
FIG. 57 is a rear perspective view of a multiple compartment cartridge to illustrate its single drain. The single drain is designed to separately dispense liquid from any of its chambers.

FIG. 57 is a rear perspective view of a multiple compartment cartridge 108 to illustrate its single drain 90. This single drain 90 can have multiple ports, where solution can be drawn from any of the desired compartments. The cartridge 108 can also have a method to internally switch a single port drain 90 with any of the compartments.

What is claimed is:

1. A liquid dispensing air freshener system, comprising:
   a) at least one liquid pump,
   b) at least one liquid inlet orifice, said orifice is in fluid connection with said pump,
   c) at least one cartridge removably coupled to said inlet orifice, comprising:
      (1) a drain valve, said valve can open to release liquid from said cartridge,
      (2) closure means with said valve for closing said valve,
   d) at least one valve actuator, whereby said actuator can open said valve when said cartridge is coupled to said orifice, and whereby liquid can be released from said cartridge to said pump,
   e) at least one evaporation chamber, said chamber is in fluid connection to said pump, whereby said chamber can receive dispensed liquid from said pump,
   f) vaporizing means within said chamber for vaporizing liquid into the ambient air,
   g) an electronic control module, said control module controls the activation of said pump,
   h) whereby said control module activates said liquid pump to dispense liquid from said cartridge to said evaporation chamber, and whereby said means for vaporizing liquid will vaporize liquid from said chamber into the ambient air.

2. The air freshener system of claim 1, further including a chassis to house said air freshener system comprising a plug which can be inserted into an electric power receptacle of a wall outlet, whereby said air freshener system can function as a wall receptacle plug-in device.

3. The air freshener system of claim 2, further including a light attached to said chassis, whereby said air freshener system can also function as a night light.

4. The air freshener system of claim 1, further including a chassis to house said air freshener system comprising a power plug adapter for motor vehicles, whereby said adapter can supply vehicle power so that said air freshener system can be used as vehicle air freshener system.

5. The air freshener system of claim 1, further including a chassis with predetermined dimensions to house said air freshener system comprising at least one internal power source, whereby said air freshener system can be self-powered in order to function as a tabletop unit and as a compact, portable, hand-held air freshener for the pocket, purse, and motor vehicle.

6. The air freshener system of claim 1, further including a chassis with predetermined dimensions to house said air freshener system in part or in total that is removably coupled to an interior panel of a newly manufactured or used motor vehicle, whereby said air freshener system can be installed into a dash panel stereo player compartment or other predetermined location so that said air freshener system can function as a vehicle air freshener system, and whereby any of said air freshener system components in part or in total is manufactured in combination with a motor vehicle.

7. The air freshener system of claim 1, further including a chassis having a bottom side, and defining an interior space, comprising:
   a) a mounting guide on said cabinet bottom side, whereby said cabinet can mount onto a toilet water tank,
   b) at least one compartment in said chassis interior space for the mounting of components,
   c) whereby said air freshener system can function as a toilet tank mounted air freshener.

8. The air freshener system of claim 1, further including a chassis with at least one user accessible evaporation chamber, whereby scent producing materials can be placed, such as fresh flowers, potpourri and perfume, and whereby said chassis allows said air freshener system to function as a dual-purpose device used to disperse said scent producing materials into the ambient air as well as liquid dispensed from said cartridge.

9. The air freshener system of claim 1, further including a cabinet subassembly, comprising:
   a) a first chassis to house said control module,
   b) at least one second chassis to house said pump and said cartridge,
   c) a combining method to modularly combine said first chassis with said second chassis,
   d) whereby said first chassis and at least one or a plurality of said second chassis can be modularly stacked together to form said cabinet for said air freshener system.

10. The air freshener system of claim 1 wherein said control module has means for controlling a plurality of liquid pumps in sequence or concurrently to dispense liquid from said cartridges to said evaporation chamber, whereby any one or combination of vapor mixture compositions can be achieved with automation and precision.

11. The air freshener system of claim 1 wherein said cartridge contains means for storing relevant specification data about the liquid that is contained within said cartridge and has means for conveying this data to said control module, whereby said control module can retrieve said data from said cartridge and use said data to enhance the operational performance of said air freshener system.

12. The air freshener system of claim 1, further including sensors for collecting data, said sensors communicate with said control module, whereby relevant data, such as from temperature and humidity sensors that can measure ambient conditions, as well as occupancy and air conditioner status sensors to enhance the operational performance of said air freshener system.

13. The air freshener system of claim 1, further including a remote control device, said device communicates with said control module, whereby said air freshener system can be remotely controlled by said device in order to operate the various features of said air freshener system.

14. The air freshener system of claim 1 wherein said cartridge contains a plurality of compartments for the purpose of storing different kinds of liquids, said cartridge has the means for dispensing said liquids without mixing them, whereby just one of said cartridge can dispense a plurality of liquids.

15. The air freshener system of claim 1 wherein said cartridge contains an internal bladder to store liquid therein, whereby said cartridge would form a protective shell for said bladder and provide a modular structure for its use in said air freshener system, and whereby liquid can be isolated from the ambient air.

16. The air freshener system of claim 1 wherein said cartridge may contain at least one liquid selected from the following list: perfumes, air fresheners, household cleaning materials, sanitizers, disinfectants, repellents, insecticides, aroma therapy formulations, medicinal, and therapeutic liquids, whereby said air freshener system can be used to dispense a wide range of solutions and whereby said air freshener system can then be used for a wide variety of purposes.

17. A liquid dispensing air freshener system, comprising:
   a) at least one liquid pump,
   b) at least one liquid inlet orifice, said orifice is in fluid connection with said pump,
   c) at least one tank removably coupled to said inlet orifice to contain liquid,
   d) at least one evaporation chamber, said chamber is in fluid connection to said pump, whereby said chamber can receive dispensed liquid from said pump,
   e) vaporizing means within said chamber for vaporizing liquid into the ambient air,
   f) an electronic control module, said control module controls the activation of said pump,
   g) whereby said control module activates said liquid pump to dispense liquid from said tank to said chamber, and whereby said means for vaporizing liquid will vaporize liquid from said chamber into the ambient air.

18. The air freshener system of claim 17, further including a chassis having a bottom side, and defining an interior space, comprising:
   a) a mounting guide on said cabinet bottom side, whereby said cabinet can mount onto a toilet water tank,
   b) at least one compartment in said chassis interior space for the mounting of components,
   c) whereby said air freshener system can function as a toilet tank mounted air freshener.

19. The air freshener system of claim 17, further including a chassis including at least one user accessible evaporation chamber, whereby scent producing materials can be placed, such as fresh flowers, potpourri or perfume, and whereby said chassis allows said air freshener system to function as a dual-purpose device used to disperse said scent producing materials into the ambient air as well as liquid dispensed from said tank.

20. The air freshener system of claim 17 wherein said control module has means for controlling a plurality of liquid pumps in sequence or concurrently to dispense liquid from said tanks to said evaporation chamber, whereby any one or combination of vapor mixture compositions can be achieved with automation and precision.

21. The air freshener system of claim 17, further including sensors for collecting data, said sensors communicate with said control module, whereby relevant data, such as from temperature and humidity sensors that can measure ambient conditions, as well as occupancy and air conditioner status sensors to enhance the operational performance of said air freshener system.

22. The air freshener system of claim 17 wherein said tank may contain at least one liquid selected from the following list: perfumes, air fresheners, household cleaning materials, sanitizers, disinfectants, repellents, insecticides, aroma therapy formulations, medicinal, and therapeutic liquids, whereby said air freshener system can be used to dispense a wide range of solutions and whereby said air freshener system can then be used for a wide variety of purposes.

23. A liquid dispensing air freshener system, comprising:
   a) at least one liquid pump,
   b) at least one liquid inlet orifice, said orifice is in fluid connection with said pump,
   c) at least one cartridge removably coupled to said inlet orifice, said inlet orifice can penetrate said cartridge while said cartridge is coupled to said inlet orifice, whereby liquid can be released from said cartridge to said pump,
   d) at least one evaporation chamber, said chamber is in fluid connection to said pump, whereby said chamber can receive dispensed liquid from said pump,
   e) vaporizing means within said chamber for vaporizing liquid into the ambient air,
   f) an electronic control module, said control module controls the activation of said pump,
   g) whereby said control module activates said liquid pump to dispense liquid from said cartridge to said chamber, and whereby said means for vaporizing liquid will vaporize liquid from said chamber into the ambient air.

* * * * *